US007542961B2

(12) United States Patent
Gogolak

(10) Patent No.: US 7,542,961 B2
(45) Date of Patent: Jun. 2, 2009

(54) METHOD AND SYSTEM FOR ANALYZING DRUG ADVERSE EFFECTS

(76) Inventor: Victor Gogolak, 934 Douglass Dr., McLean, VA (US) 22101

( * ) Notice: Subject to any disclaimer, the term of this patent is extended or adjusted under 35 U.S.C. 154(b) by 623 days.

(21) Appl. No.: 09/681,585

(22) Filed: May 2, 2001

(65) Prior Publication Data

US 2002/0165852 A1    Nov. 7, 2002

(51) Int. Cl.
G06F 15/18    (2006.01)
G06F 15/00    (2006.01)
A61K 49/00   (2006.01)
G06F 7/00    (2006.01)
G06F 17/30   (2006.01)

(52) U.S. Cl. .......................... 706/62; 424/10.1; 707/3; 706/924

(58) Field of Classification Search ............... 706/11, 706/45, 924, 62; 705/2, 3; 707/3, 1, 9–10, 707/102, 104.1; 424/10.1; 717/1, 3, 9–10, 717/102, 104.1
See application file for complete search history.

(56) References Cited

U.S. PATENT DOCUMENTS

| | | | |
|---|---|---|---|
| 5,299,121 A | 3/1994 | Brill et al. ............... | 364/413.01 |
| 5,337,919 A | 8/1994 | Spaulding et al. ........... | 221/2 |
| 5,371,807 A | 12/1994 | Register et al. .............. | 382/14 |
| 5,495,604 A | 2/1996 | Harding et al. ............. | 395/600 |
| 5,502,576 A | 3/1996 | Ramsay et al. .............. | 358/444 |
| 5,583,758 A | 12/1996 | McIlroy et al. .............. | 395/202 |
| 5,592,668 A | 1/1997 | Harding et al. ............. | 395/602 |
| 5,594,637 A | 1/1997 | Eisenberg et al. .......... | 395/202 |
| 5,634,053 A | 5/1997 | Noble et al. ................ | 395/604 |

(Continued)

FOREIGN PATENT DOCUMENTS

| | | |
|---|---|---|
| JP | 10-225500 | 8/1998 |
| JP | 11-282934 | 10/1999 |

OTHER PUBLICATIONS

Ng et al, "An Intelligent Agent for Web Advertisements", International Symposium on Cooperative Database Systems for Advance Applications, Apr. 23-24, 2001.*

(Continued)

Primary Examiner—David R Vincent
Assistant Examiner—Benjamin Buss
(74) Attorney, Agent, or Firm—Morrison & Foerster LLP

(57) ABSTRACT

The system of the present invention for assessing and analyzing the risks of adverse effects resulting from the use of at least one substance of interest, comprises a selector for identifying at least one substance of interest; a profiler for selecting from multiple profiles related to the safety of the at least one substance of interest, using at least one filter; at least one data mining engine; and an output device for displaying the analytic results from the data mining engine. Preferably, the at least one data mining engine is selected from (1) a proportional analysis engine to assess deviations in a set of the reactions to the drug of interest; (2) a comparator to measure the reactions to the drug of interest against a user-defined backdrop, and (3) a correlator to look for correlated signal characteristics in drug/reaction/demographic information; and an output device whereby a user can receive analytic results from the selector, the proportional analysis engine, the comparator, and the correlator.

35 Claims, 24 Drawing Sheets

U.S. PATENT DOCUMENTS

| | | | | |
|---|---|---|---|---|
| 5,642,731 | A | 7/1997 | Kehr | 128/630 |
| 5,664,109 | A | 9/1997 | Johnson et al. | 705/2 |
| 5,692,171 | A | 11/1997 | Andres | 395/601 |
| 5,737,539 | A | 4/1998 | Edelson et al. | 395/203 |
| 5,758,095 | A | 5/1998 | Albaum et al. | 395/202 |
| 5,804,803 | A | 9/1998 | Cragun et al. | 235/375 |
| 5,833,599 | A | 11/1998 | Schrier et al. | 600/300 |
| 5,845,255 | A | 12/1998 | Mayaud | 705/3 |
| 5,860,917 | A | 1/1999 | Comanor et al. | 600/300 |
| 5,864,789 | A | 1/1999 | Lieberman et al. | 704/9 |
| 5,911,132 | A | 6/1999 | Sloane | 705/3 |
| 5,924,074 | A | 7/1999 | Evans | 705/3 |
| 6,000,828 | A | 12/1999 | Leet | 364/401 |
| 6,014,631 | A | 1/2000 | Teagarden et al. | 705/3 |
| 6,067,524 | A | 5/2000 | Byerly et al. | 705/3 |
| 6,076,083 | A | 6/2000 | Baker | 706/52 |
| 6,076,088 | A | 6/2000 | Paik et al. | 707/5 |
| 6,082,776 | A | 7/2000 | Feinberg | 283/72 |
| 6,108,635 | A | 8/2000 | Herren et al. | 705/2 |
| 6,120,443 | A | 9/2000 | Cohen-Laroque | 600/300 |
| 6,137,911 | A | 10/2000 | Zhilyaev | 382/225 |
| 6,151,581 | A | 11/2000 | Kraftson et al. | 705/3 |
| 6,219,674 | B1* | 4/2001 | Classen | 707/104.1 |
| 6,226,564 | B1 | 5/2001 | Stuart | 700/231 |
| 6,263,329 | B1 | 7/2001 | Evans | 707/3 |
| 2002/0073042 | A1* | 6/2002 | Maritzen et al. | 705/64 |
| 2002/0142815 | A1* | 10/2002 | Candelore | 463/1 |
| 2004/0015372 | A1* | 1/2004 | Bergman et al. | 705/3 |
| 2004/0030503 | A1* | 2/2004 | Arouh et al. | 702/20 |

OTHER PUBLICATIONS

Szarfman, Ana, M.D., Ph.D., "New Methods for Signal Detection," Proceedings of the 15$^{th}$ International Conference on Pharmacoepidemiology, 56 pp., Aug. 28, 1999.*

Karel,M. "Tasks of Food Technology in the 21st Century" FoodTechnology. vol. 54, No. 6; Jun. 2000.*

Guo,J.J. et al. "Comparison and Analysis of the National Drug Code Systems Among Drug Information Databases" Drug Information Journal vol. 32. 1998.*

Stead, W.W. et al. "Integration and Beyond: Linking Information from Disparate Sources and into Workflow" Journal of the American Medical Informatics Association vol. 7 No. 2. Mar./Apr. 2000.*

Szarfman, Ana, M.D., Ph.D., "New Methods for Signal Detection," Proceedings of the 15th International Conference on Pharmacoepidemiology, 56 pp., Aug. 28, 1999.*

Friedman,M.A. et al. "The Safety of Newly Approved Medicines: Do Recent Market Removals Mean There Is a Problem?" Journal of teh American Medical Association (JAMA), vol. 281, No. 18, pp. 1728-1734. May 12 1999.*

Omoigui,N.A. et al. "Observational versus Randomized Medical Device Testing Before and After Market Approval—The Atherectomy-versus-angioplasty Controversy" Controlled Clinical Trials 16:143-149, Elsevier Science Inc. 1995.*

Multum Trusted Health Information [online], [retrieved on Aug. 22, 2002], 1 p., Retrieved from the Internet: http://www.multum.com.

Epocrates [online], Copyright 2002 [retrieved on Aug. 22, 2002], 1 p., Retrieved from the Internet: http://www.epocrates.com.

PDR.net [online], Copyright 2002 [retrieved on Aug. 22, 2002], 1 p., Retrieved from the Internet: http//www.pdr.net/HomePage_template.jsp.

"VAERS Data: Guide to Interpreting Case Report Information Obtained From the Vaccine Adverse Event Reporting System (VAERS)" [online], [retrieved on Jun. 11, 2002, 2 pp., Retrieved from the Internet: http://www.vaers.org/info.

Szarfman, Ana, M.D., Ph.D., "Application of Screening Algorithms and Computer Systems to Efficiently Signal Combinations of Drugs and Events in FDA's Spontaneous Reports" [online], Oct. 22, 2001, 2pp., Retrieved from the Internet: http://apha.confex.com/apha/129.am/techprogram/paper_32272.

"Vaccine Adverse Event Reporting System (VAERS)" [online], U.S. Department of Health and Human Services, Jul. 2001 [retrieved Jul. 2001], 12 pp., Retrieved from the Internet: http://www.vaers.org/search/README.

Andrews, Michelle, "Prescription for Disaster," *SmartMoney*, pp. 124-129, May 2001.

Mootrey, Gina, et al., "Chapter 18: Surveillance for Adverse Events Following Vaccination," *VPD Surveillance Manual*, 20 pp., 1999.

Szarfman, Ana, M.D., Ph.D., "New Methods for Signal Detection," *Proceedings of the 15$^{th}$ International Conference on Pharmacoepidemiology*, 56 pp., Aug. 28, 1999.

DuMouchel, William, "Bayesian Data Mining in Large Frequency Tables, with an Application to the FDA Spontaneous Reporting System," *The American Statistician*, vol. 53, No. 3., 31 pp., Apr. 1999.

"The Totally Unauthorized, Completely Repudiated, Bootlegged, Unsupported, Undocumented, Insider's Post-Pre-Alpha Guide to Multum's Lexicon," Multum Information Services, Inc., pp. 1-49, Copyright 1997-1999, Apr. 12, 1999 (Rev. 3.d).

"Post-Marketing Surveillance for Adverse Events After Vaccination: The National Vaccine Adverse Event Reporting System (VAERS)," *Medwatch*, 12 pp., Nov. 1998.

"Multum Releases Web-Based MediSource Lexicon; Downloadable Drug Product and Disease Listings Database," *PR Newswire*, 2 pp., Apr. 10, 1997.

Lipschutz, Seymour, Ph.D., "Theory and Problems of Linear Algebra," Schaum's Outline Series, McGraw-Hill Book Company, 5 pp., 1968.

Anderson, T. W., "A Bibliography of Multivariate Statistical Analysis," Oliver & Boyd, Edinburgh, 3 pp., 1972.

Darlington, Richard B., "Regression and Linear Models," McGraw-Hill Publishing Company, 15 pp., 1990.

Press, James S. and Wilson, Sandra, "Choosing Between Logistic Regression and Discriminant Analysis," *Journal of the American Statistical Association*, vol. 73, pp. 699-705, Dec. 1978.

Kosko, Bart, "Neural Networks and Fuzzy Systems—A Dynamical Systems Approach to Machine Intelligence," Prentice Hall, Englewood Cliffs, NJ, 11 pp., 1992.

International Search Report for Application No. PCT/US02/13666, dated Jul. 16, 2002 (mailing date).

International Search Report for Application No. PCT/US02/13662, dated Jul. 15, 2002 (mailing date).

* cited by examiner

FILTER SCREEN

| | SEARCH CRITERIA DETAILS | |
|---|---|---|
| • SUMMARY | SEARCH CRITERIA NAME: ALENDRONATE0396 | |
| | (DRUG LEGEND: A=ALL, S=SUSPECT, I=INGREDIENT, N=DRUG NAME) | |
| DRUGS (DETAILS) | CRITERIA | VALUE |
| REACTIONS (DETAILS) | INCLUDED INGREDIENTS | ALENDRONATE SODIUM (A) |
| DEMOGRAPHICS | DRUG BOOLEAN | [ (ALENDRONATE SODIUM) ]  [CONCOMITANT OFF] |
| REPORT DATES | REACTIONS | ALL [INCLUDED] |
| EVENT DATES | DEMOGRAPHICS | ALL |
| OUTCOMES | REPORT DATES | FROM: FEB 1, 1969 TO: MAR 6, 1996 |
| REPORT SOURCES | EVENT DATES | ALL |
| REPORT TYPES | INCLUDED OUTCOMES | CONGENITAL ANOMALY; DEATH; DISABILITY |
| CASE SOURCES | REPORT SOURCES | ALL |
| EXCLUDED CASES | REPORT TYPES | ALL |
| EXCLUDED DUPLICATE CASES | CASE SOURCES | ALL |
| NOTES | EXCLUDED CASES | NONE |
| | EXCLUDED DUPLICATE CASES | OFF |

FIG. 4

503 (THERAPEUTIC CATEGORY)
500 (GENERIC, OR 'INGREDIENT')
501 (TRADE NAME)

QUERY SCREEN

SEARCH BY DRUG: ⦿ INGREDIENT ○ NAME  [          ] (SEARCH)
SEARCH BY CATEGORY: [ACE INHIBITORS (4)    ▼] (SEARCH)

4 TRADE(S) MATCHED

| INGREDIENTS (ALL, SUSPECT) | NAMES (SHOW ALL NAMES) |
|---|---|
| ENALAPRIL MALEATE (1,0) SHOW SOURCE... | ☐ ENALAPRIL MALEATE TABLETS (1,0) |
| LISINOPRIL (13,8) SHOW SOURCE... | ☐ LISINOPRIL TABLETS (12,8)<br>☐ PRINIVIL TABLETS (1,0) |
| HYDROCHLOROTHIAZIDE, TELMISARTAN (0,0) SHOW SOURCE... | ☐ MICARDIS HCT TABLETS (0,0) |

TO VIEW DRUG LIST AND DEFINE LOGICAL RULES, CLICK "DETAILED SETUP".

NO. OF INGREDIENTS SELECTED  [ 0 ]
NO. OF DRUGS SELECTED  [ 0 ]

REVIEW SELECTION AND SET DETAILED OPTIONS  (DETAILED SETUP)

FIG.5

DATA PEDIGREE SCREEN

| 600<br>MAPTO | 601<br>VERBATIM | 602<br>SOURCE | 603<br>INCIDENTS | 604<br>CASE COUNTS | 605<br>PROCESSING | 606<br>CROSS REFERENCE | 607<br>FIRST/LAST |
|---|---|---|---|---|---|---|---|
| PROZAC | PROZAC | SRS | 47953 | 47953 | A | ORANGE BOOK | 4/27/69-12/2/97 |
| PROZAC | PROZAC | AERS | 3309 | 3309 | A | ORANGE BOOK | 11/1/69-6/29/99 |
| PROZAC | PROZAC (FLUOX) | AERS | 2 | 2 | M | NDCD | 2/27/69-2/2/97 |
| FLUOXETINE | FLUOXETINE HCL | AERS | 122 | 122 | M | ORANGE BOOK | 6/27/69-1/2/97 |
| ETC.... | | | | | | | |

FIG.6

| CONCOMITANT DRUGS | SUSPECT | | NON-SUSPECT | | | FILTER... |
|---|---|---|---|---|---|---|
| TOP 10 DRUGS | S | NS | S | NS | TOTAL | % |
| HYDROCHLOROTHIAZIDE | 9 | 36 | 0 | 0 | 45 | 10.79% |
| ASPIRIN | 2 | 38 | 0 | 5 | 45 | 10.79% |
| FUROSEMIDE | 2 | 32 | 0 | 1 | 35 | 8.39% |
| DIGOXIN | 0 | 30 | 0 | 0 | 30 | 7.19% |
| AMLODIPINE BESYLATE | 0 | 24 | 4 | 0 | 28 | 6.71% |
| ENALAPRIL MALEATE | 4 | 15 | 0 | 5 | 24 | 5.76% |
| VERAPAMIL HYDROCHLORIDE | 11 | 10 | 0 | 2 | 23 | 5.52% |
| ESTROGENS, CONJUGATED | 0 | 23 | 0 | 0 | 23 | 5.52% |
| METOPROLOL SUCCINATE | 8 | 11 | 0 | 3 | 22 | 5.28% |
| METOPROLOL TARTRATE | 0 | 15 | 0 | 7 | 22 | 5.28% |

| SUSPECT TOTAL | NON-SUSPECT TOTAL | TOTAL |
|---|---|---|
| 172 | 1141 | 1313 |

MORE DETAILS...

| Age Group | Male | Female | Unknown | Total | % |
|---|---|---|---|---|---|
| >75 | 18 | 73 | 0 | 91 | 21.82% |
| 51-75 | 89 | 123 | 1 | 213 | 51.08% |
| 31-50 | 30 | 16 | 0 | 46 | 11.03% |
| 16-30 | 2 | 1 | 0 | 3 | 0.72% |
| <16 | 0 | 0 | 0 | 0 | 0.00% |
| Unknown | 11 | 30 | 23 | 64 | 15.35% |
| Total | 150 | 243 | 24 | 417 | |
| % | 35.97% | 58.27% | 5.76% | | |

Demographics — filter more details

Figure 11

| Outcomes | | |
|---|---|---|
| Outcome | Count | % |
| DEATH | 36 | 7.19% |
| DISABILITY | 18 | 3.59% |
| HOSPITALIZATION - INITIAL OR PROLONGED | 231 | 46.11% |
| LIFE-THREATENING | 46 | 9.18% |
| OTHER | 168 | 33.53% |
| REQUIRED INTERVENTION TO PREVENT PERMANENT IMPAIRMENT/DAMAGE | 2 | 0.40% |

| Total serious outcomes | Total non-serious outcomes | Total outcomes |
|---|---|---|
| 333 | 168 | 501 | more details

REACTION FILTER SCREEN

SEARCH REACTION: [        ]  (FIND NEXT) (RESET) (INVERT REACTIONS) (COLLAPSE REACTION TREE) (DETAILED SETUP)

■ REACTIONS

⊟ ■ [SOC] BLOOD AND LYMPHATIC SYSTEM DISORDERS
    ⊞ ☑ [HLGT] ANAEMIAS NONHAEMOLYTIC AND MARROW DEPRESSION
    ⊟ ■ [HLGT] BLEEDING TENDENCIES AND PURPURAS (EXCL THROMBOCYTOPENIC)
        ⊟ ■ [HLT] BLEEDING TENDENCIES
            ☐ [PT] BLEEDING TENDENCY
            ☐ [PT] HAEMORRHAGIC DISEASE OF NEWBORN
            ☑ [PT] HAEMORRHAGIC DISORDER
        ⊞ ☑ [HLT] PURPURAS (EXCL THROMBOCYTOPENIC)
    ⊞ ☑ [HLGT] COAGULOPATHIES AND BLEEDING DIATHESES
    ⊞ ☑ [HLGT] HAEMATOLOGICAL DISORDERS NEC
    ⊞ ☑ [HLGT] HAEMATOPOIETIC NEOPLASMS (EXCL LEUKAEMIAS AND LYMPHOMAS)
    ⊞ ☑ [HLGT] HAEMOGLOBINOPATHIES
    ⊞ ☑ [HLGT] HAEMOLYSES AND RELATED CONDITIONS
    ⊞ ☑ [HLGT] LEUKAEMIAS
    ⊞ ☑ [HLGT] PLATELET DISORDERS
    ⊞ ☑ [HLGT] RED BLOOD CELL DISORDERS
    ⊞ ☑ [HLGT] SPLEEN, LYMPHATIC AND RETICULOENDOTHELIAL SYSTEM DISORDERS
    ⊞ ☑ [HLGT] WHITE BLOOD CELL DISORDERS
⊞ ☑ [SOC] CARDIAC DISORDERS
⊞ ☑ [SOC] CONGENITAL, FAMILIAL AND GENETIC DISORDERS

FIG. 12

CORRELATION SCREEN

| KEY | CATEGORY | TERM 1 | TERM 2 | CATEGORY | SCORE | CASE COUNTS | DF | CONFIDENCE LEVEL | RANK |
|---|---|---|---|---|---|---|---|---|---|
| ⊟ ·· CANDESARTAN CILEXETIL | | | | | 0.7283 | 2557 | 12317364 | 99.99 | |
| ⊟ ·· SEX | | | | | 0.7283 | 2557 | 12317364 | 99.99 | |
|    FEMALE | DRUGS | CANDESARTAN CILEXETIL | FEMALE | SEX | 0.7283 | 2557 | 12317364 | 99.99 | 1 |
|    MALE | DRUGS | CANDESARTAN CILEXETIL | MALE | SEX | 0.6481 | 2025 | 9753656 | 99.98 | 14 |
|    SEX NOT SPECIFIED | DRUGS | CANDESARTAN CILEXETIL | SEX NOT SPECIFIED | SEX | 0.2222 | 238 | 1142103 | 99.96 | 234 |
| ⊟ ·· DEMOGRAPHICS | | | | | 0.7190 | 2492 | 12004129 | 99.99 | ... |
|    AGE 51 TO 75 YEARS | DRUGS | CANDESARTAN CILEXETIL | AGE 51 TO 75 YEARS | DEMOGRAPHICS | 0.7190 | 2492 | 12004129 | 99.99 | 2 |
|    AGE OVER 75 YEARS | DRUGS | CANDESARTAN CILEXETIL | AGE OVER 75 YEARS | DEMOGRAPHICS | 0.4591 | 1016 | 4891285 | 99.97 | 23 |
|    AGE NOT SPECIFIED | DRUGS | CANDESARTAN CILEXETIL | AGE NOT SPECIFIED | DEMOGRAPHICS | 0.3986 | 766 | 3686535 | 99.97 | 45 |
|    AGE 31 TO 50 YEARS | DRUGS | CANDESARTAN CILEXETIL | AGE 31 TO 50 YEARS | DEMOGRAPHICS | 0.3243 | 507 | 2438414 | 99.97 | 67 |

RED ☒ YELLOW ▨ ORANGE

FIG.13

CORRELATION DETAILS
ANALYZED DRUG: CANDESARTAN CILEXETIL
CASES FOR TERM PAIR: RENAL FUNCTION ANALYSES [OTHER REACTION]/RENAL FAILURE AND IMPAIRMENT [OTHER REACTION]

CASES 1 TO 18 OF 18 CASES

| | CASE ID | SEX | MANUFACTURER CONTROL CODE | FDA REPORT RECEIPT DATE | AGE | DRUGS | REACTIONS | SERIOUS |
|---|---|---|---|---|---|---|---|---|
| | 1401 | 1402 | 1403 | 1404 | 1405 | 1406 | 1407 | 1408 |
| 1 | 3263641 | F | 19990300088 | 1999-06-17 | 74 | ATACAND | BLOOD CREATININE INCREASED; DIALYSIS Nos; RENAL FAILURE AGGRAVATED | N |
| 2 | 3198047 | F | 19990200143 | 1999-03-12 | 57 | ACURETIC, ATORVASTATIN, ATACAND, CEFIXIME, NITRO-DUR, TERBASMIN EXPECTORANTE | BLOOD CREATININE INCREASED; BLOOD UREA INCREASED; HYPOTENSION Nos; RENAL FAILURE ACUTE | Y |
| 3 | 3171644 | F | 19981100002 | 1999-01-17 | 69 | XANAX, ACETYLSALICYLIC ACID, WELLBUTRIN, ATACAND, ARTHROTEC, DIGOXIN, LEVAQUIN, CLARITIN, ANTIVERT, PYRIDIUM, ZOLOFT, DYAZIDE, VERAPAMIL-SLOW RELEASE, AMBIEN | ABDOMINAL PAIN Nos; BLOOD CREATININE INCREASED; BLOOD UREA INCREASED; CORONARY ARTERY DISEASE Nos; HAEMOPTYSIS; HEART RATE INCREASED; HYPERTENSION AGGRAVATED; RENAL FAILURE ACUTE | N |

FIG.14

CASE DETAILS SCREEN

| | | | | | |
|---|---|---|---|---|---|
| 1501 — CASE ID: | 3641306 | | | | |
| 1502 — SEX: | F | | | | |
| 1503 — AGE: | 14 YEARS 0 MONTHS | | | | |
| WEIGHT: | NONE. | | | | |
| DEATH DATE: | NONE. | | | | |

1504 — REACTIONS:

| AS REPORTED | ONSET DATE | PREFERRED TERM |
|---|---|---|
| NAIL DISCOLOURATION | --- | NAIL DISCOLOURATION |
| TOOTH DISCOLOURATION | --- | TOOTH DISCOLOURATION |
| TREMOR NEC | --- | TREMOR |

1505 — CONCOMITANT DRUGS:

| AS REPORTED | NAME | DOSE | ROUTE | DRUG ROLE |
|---|---|---|---|---|
| ATACAND | ATACAND | 16 MG QD PO | ORAL | PRIMARY SUSPECT DRUG |
| ATACAND | ATACAND | 12 MG QD PO | ORAL | SECONDARY SUSPECT DRUG |

| | |
|---|---|
| 1506 — OUTCOME: | OTHER(OT) |
| 1509 — EVENT DATE: | NONE. |
| SENDING MANUFACTURER | ASTRAZENECA PHARMACEUTICALS LP |
| 1507 — MANUFACTURER CONTROL CODE: | 20000900273 |
| 1508 — MANUFACTURER DATE: | 12 SEP 2000 |
| 1510 — REPORT CODE: | PERIODIC |
| 1511 — REPORT SOURCE: | HEALTH PROFESSIONAL |
| 1512 — CASE SOURCE: | |
| 1513 — NARRATIVE: | NONE. |

FIG. 15

CORRELATOR DISPLAY SCREENS

COLUMN DISPLAY

| KEY | CATEGORY | TERM 1 | TERM 2 | CATEGORY | SCORE |
|---|---|---|---|---|---|
| ⊟···CANDESARTAN CILEXETIL | | | | | 0.7283 |
| ⊟···SEX | | | | | 0.7283 |
| FEMALE | DRUGS | CANDESARTAN CILEXETIL | FEMALE | SEX | 0.7283 |
| MALE | DRUGS | CANDESARTAN CILEXETIL | MALE | SEX | 0.6461 |
| SEX NOT SPECIFIED | DRUGS | CANDESARTAN CILEXETIL | SEX NOT SPECIFIED | SEX | 0.2222 |
| ⊟···DEMOGRAPHICS | | | | | 0.7190 |
| AGE 51 TO 75 YEARS | DRUGS | CANDESARTAN CILEXETIL | AGE 51 TO 75 YEARS | DEMOGRAPHICS | 0.7190 |
| AGE OVER 75 YEARS | DRUGS | CANDESARTAN CILEXETIL | AGE OVER 75 YEARS | DEMOGRAPHICS | 0.4591 |
| AGE NOT SPECIFIED | DRUGS | CANDESARTAN CILEXETIL | AGE NOT SPECIFIED | DEMOGRAPHICS | 0.3966 |
| AGE 31 TO 50 YEARS | DRUGS | CANDESARTAN CILEXETIL | AGE 31 TO 50 YEARS | DEMOGRAPHICS | 0.3243 |
| AGE 16 TO 30 YEARS | DRUGS | CANDESARTAN CILEXETIL | AGE 16 TO 30 YEARS | DEMOGRAPHICS | 0.0827 |
| AGE UNDER 16 YEARS | DRUGS | CANDESARTAN CILEXETIL | AGE UNDER 16 YEARS | DEMOGRAPHICS | 0.0352 |
| ⊞···OUTCOMES | | | | | 0.6639 |
| ⊞···DRUGS | | | | | 0.3824 |
| ⊟···REACTIONS | | | | | 0.2452 |
| DIZZINESS | DRUGS | CANDESARTAN CILEXETIL | DIZZINESS 75 YEARS | REACTIONS | 0.2452 |
| NAUSEA | DRUGS | CANDESARTAN CILEXETIL | NAUSEA 75 YEARS | REACTIONS | 0.2121 |
| HYPERTENSION NOS | DRUGS | CANDESARTAN CILEXETIL | HYPERTENSION NOS | REACTIONS | 0.2116 |

▨ RED  ▨ YELLOW  ▨ ORANGE  ▤ PURPLE  ▥ GREEN

FIG.16A

PROPORTIONAL DISPLAY SCREEN: MATRIX

PROPORTIONAL ANALYSIS RESULTS

PROPORTIONAL ANALYSIS
NAME: RMETHSUSP
DATE SAVED: 19 AUG 2005 19:18:36
DATA SET: FDA SRS/AERS COMBINED DATA-Q1 2005
TOTAL CASE COUNT: 5478  (PROFILE CASE LIST)  NOTES: [NO NOTES TO DISPLAY]

| INGREDIENTS | TRADE NAME |
|---|---|
| METHADONE | |
| METHADONE HYDROCHLORIDE | |

INPUT PARAMETERS: (VIEW SETUP) (SAVE SETUP) (MODIFY SETUP)
CURRENT SCREEN: (MODIFY DISPLAY) (CHART RESULTS) (REPORT RESULTS)

PRIMARY DIMENSION: [REACTION ▾]  VIEW: [SOC ▾]  (EXPAND TO VIEW)  SECONDARY DIMENSION: [-NONE- ▾]  VIEW: [-NONE- ▾]

Legend: ▨ >3  ▩ 2  ▨ 3  ▦ .5  ▦ .333  ▦ .8  ▨ 1.25

| SOC\|HLGT\|HLT\|PT ▸ | REACTION ◆ | OBSERVED ◆ COUNT | PRR- EXPECTED ◆ COUNT | PROPORTIONAL REPORT RATIO (PRR) | | | | PRR- CHI- ◆ SQUARE | PRR- CONFIDENCE ◆ LEVEL |
|---|---|---|---|---|---|---|---|---|---|
| | | | | SOC | HGLT | HLT | PT | | |
| ⊞...[SOC]1 | BLOOD AND LYMPHATIC SYSTEM DISORDERS | 89 | 343.66 | 0.26 | 1.73 | 32.34 | 44.18 | 188.7 | 9 |
| ⊞...[SOC]2 | CARDIAC DISORDERS | 916 | 537.25 | 1.70 | 3.87 | 27.67 | 86.25 | 267.0 | 9 |
| ⊞...[SOC]3 | CONGENITAL, FAMILIAL AND GENETIC DISORDERS | 161 | 49.59 | 3.25 | 6.64 | 10.98 | 301.87 | 250.3 | 9 |
| ⊞...[SOC]4 | EAR AND LABYRINTH DISORDERS | 12 | 60.27 | 0.20 | 0.23 | 0.60 | 6.04 | 38.7 | 9 |
| ⊞...[SOC]5 | ENDOCRINE DISORDERS | 17 | 33.03 | 0.51 | 1.61 | 5.66 | 301.87 | 7.8 | 9 |
| ⊞...[SOC]6 | EYE DISORDERS | 72 | 256.35 | 0.28 | 2.25 | 3.17 | 19.48 | 132.6 | 9 |
| ⊞...[SOC]7 | GASTROINTESTINAL DISORDERS | 391 | 1108.19 | 0.35 | 1.46 | 17.76 | 60.37 | 464.1 | 9 |

FIG. 17

COMPARATOR AND PRE-POST DETAILS SCREEN

| SOC\|HLGT\|HLT\|PT ⇔ | REACTIONS ⇔ | CLINICAL TRIAL ⇔ REACTION | POST MARKET ⇔ REACTION | REACTION COUNT DIFF ⇔ (B-A) | REACTION COUNT RATIO (B/A) | % OF REACTIONS ⇔ FROM A | % OF REACTIONS ⇔ FROM B | % OF REACTIONS ⇔ DIFF (B-A) | % OF REACTIONS ⇔ RATIO (B/A) |
|---|---|---|---|---|---|---|---|---|---|
| ▼⊟⋯[HLT] 7.12.7 | NAUSEA AND VOMITING SYMPTOMS | 710 | 562 | -148 | 1 | 7.10 | 4.45 | -2.65 | 0.63 |
| [PT] 7.12.7.2 | NAUSEA | 360 | 406 | 46 | 2 | 3.60 | 3.22 | -0.38 | 0.89 |
| [PT] 7.12.7.6 | VOMITING NOS | 100 | 156 | 56 | 2 | 1.00 | 1.24 | 0.24 | 1.24 |
| [PT] 7.12.7.4 | REGURGITATION OF FOOD | 250 | 0 | -250 | 0 | 2.50 | 0.00 | -2.50 | 0.00 |
| ▼⊞⋯[HLT] 7.12.4 | FLATULENCE, BLOATING AND DISTENSION | 360 | 509 | 149 | 1 | 3.60 | 4.03 | 0.43 | 1.12 |
| ▼⊞⋯[HLT] 7.12.2 | DYSEPTIC SIGNS AND SYMPTOMS | 360 | 486 | 126 | 1 | 3.60 | 3.85 | 0.25 | 1.07 |
| ▼⊞⋯[HLT] 7.11.1 | DIARRHOEA (EXCL INFECTIVE) | 310 | 400 | 90 | 1 | 3.10 | 3.17 | 0.07 | 1.02 |
| ▼⊞⋯[HLT] 7.10.4 | OESOPHAGITIS (EXCL INFECTIVE) | 57 | 360 | 303 | 6 | 0.57 | 2.85 | 2.28 | 5.00 |

| REACTIONS | % OF REACTIONS FROM A | % OF REACTIONS FROM B |
|---|---|---|
| HAEMOGLOBINOPATHIES | 0.00 | 0.00 |
| CHROMOSOMAL ABNORMALITIES AND ABNORMAL GENE CARRIERS | 0.00 | 0.00 |
| EAR AND LABYRINTHINE DISORDERS CONGENITAL | 0.00 | 0.01 |
| RESPIRATORY DISORDERS CONGENITAL | 0.00 | 0.01 |
| IMMUNODEFICIENCY SYNDROMES | 0.00 | 0.00 |
| CHLAMYDIAL INFECTIOUS DISORDERS | 0.00 | 0.01 |
| ECTOPARASITIC DISORDERS | 0.00 | 0.00 |

2010 points to HAEMOGLOBINOPATHIES row; 2011 points to RESPIRATORY DISORDERS CONGENITAL row.

| REACTIONS | % OF REACTIONS FROM A | % OF REACTIONS FROM B |
|---|---|---|
| BLEEDING TENDENCIES AND PURPURAS (EXCL THROMBOCYTOPENIC) | 0.01 | 0.00 |
| HAEMOGLOBINOPATHIES | 0.00 | 0.00 |
| CHROMOSOMAL ABNORMALITIES AND ABNORMAL GENE CARRIERS | 0.00 | 0.00 |
| EYE DISORDERS CONGENITAL | 0.02 | 0.00 |
| IMMUNE SYSTEM DISORDERS CONGENITAL | 0.01 | 0.00 |
| IMMUNODEFICIENCY SYNDROMES | 0.00 | 0.00 |
| ANCILLARY INFECTIOUS TOPICS | 0.01 | 0.00 |

2013 points to HAEMOGLOBINOPATHIES row; 2014 points to the % OF REACTIONS FROM A column.

FIG. 20C

CASE LIST SCREEN

| CASE ID 2100 | SEX 2101 | MANUFACTURER CONTROL CODE 2102 | FDA REPORT RECEIPT DATE 2103 | AGE 2104 | DRUGS 2105 | REACTIONS 2106 | SERIOUSNESS 2107 | REPORTING COUNTRY |
|---|---|---|---|---|---|---|---|---|
| 3319323 | M | 105204 | 1999/08/05 | 28 | INVIRASE, RITONAVIR, ZERIT, HIVID, ZIDOVUDINE, NELFINAVIR MESYLATE, VIDEX, SULFAMETHOXAZOLE + TRIMETHOPRIM, ANTICOAGULANT, HIVID | BLEEDING TENDENCY, COAGULATION FACTOR VIII LEVEL DECREASED, ECCHYMOSIS, HAEMARTHROSIS, HEADACHE, LIVER FUNCTION TEST ABNORMAL, PLATELET COUNT DECREASED, RED BLOOD CELL COUNT DECREASED, SUBDURAL HAEMATOMA, WHITE BLOOD CELL COUNT DECREASED | HOSPITALIZATION-INITIAL OR PROLONGED | |
| 3457806 | M | 10221083 | 2000/02/14 | -1 | ZERIT, EPIVIR, NORVIR, INVIRASE, CRIXIVAN, ANTIHEMOPHILIC FACTOR VIII (HUMAN) | BLEEDING TENDENCY, HAEMATOCRIT DECREASED, HAEMOGLOBIN DECREASED, HEPATIC FUNCTION ABNORMAL Nos, TRANSAMINASES INCREASED | HOSPITALIZATION-INITIAL OR PROLONGED | |
| 3489636 | M | 233093 | 2000/04/18 | 35 | INVIRASE, ZERIT, EPIVIR, NORVIR | BLEEDING TENDENCY, HAEMATOCRIT DECREASED, HAEMORRHAGE Nos, ARTHROPATHY Nos, RED BLOOD CELL COUNT DECREASED, THROMBOCYTHAEMIA | OTHER | |

FIG.21

METHOD AND SYSTEM FOR ANALYZING DRUG ADVERSE EFFECTS

BACKGROUND OF INVENTION

1. Field of the Invention

The present invention relates to a system and method for assessing and analyzing the risks of adverse effects resulting from the use of a particular drug, either alone or in combination with other drugs, nutrients, supplements, and other substances.

2. Description of the Related Art

In September 1997, information regarding cardiopulmonary disease related to the use of fenfluramine and phentermine ("fenphen") prompted the United States Food and Drug Administration (FDA) to request the manufacturers of these drugs to voluntarily withdraw both treatments for obesity from the market. Subsequent studies show a 25 percent incidence of heart valve disease apparently resulting from diet drug use. Thus, up to 1,250,000 people may have sustained heart valve damage from these diet drugs and the FDA indicates that this may be the largest adverse drug effect the agency has ever dealt with.

Current estimates are that some 2.2 million hospital patients had serious adverse drug reactions and more than 100,000 people die each year from adverse reactions to prescription drugs. Accordingly, federal officials have recommended that the FDA require hospitals to report all serious drug reactions to the agency. The Inspector General of the Department of Health and Human Services has also indicated that the FDA should also work to identify harmful effects of new drugs and encourage health-care providers to rapidly call the FDA with information about drug side effects. As new drugs are introduced at increasing rates, the FDA will likely need additional resources to protect the public from hazardous drug side effects.

If one or two adverse drug reactions slip through the FDA's reporting process, the results can be tragic for some patients. That is especially true when the adverse reactions are rare but serious—such as in the case of liver failure caused by medication. All drugs have the potential to harm or kill the people they are designed to help. An injection of penicillin can kill in minutes if the recipient is allergic to this life-saving drug. Even common aspirin can be deadly.

Clinical trials of a new drug often involve a few hundred patients and therefore may not reveal that a drug can cause serious injury or death in one patient in 10,000 or even 1,000 patients. Accordingly, it is critical for researchers and drug companies to be able to analyze and predict adverse reactions among patients in their studies.

In addition, in clinical trials for drugs used to treat diseases such as diabetes, which affects so many people and is difficult to treat, FDA officials often face tremendous pressure to accelerate their approval process. Often, in this "fast-track" process, cases of adverse drug effects may slip through reporting procedures.

An even bigger challenge to the FDA is the occurrence of adverse drug reactions after the drug is on the market. In this case the drug is prescribed to a much larger population of patients, many of whom are taking other substances such as extracts, nutrients, vitamins, hormones or drugs that might have an adverse effect with the prescribed drug.

Thus, there is a need for effective analysis of adverse drug effects.

Unfortunately, such a system has not been available.

U.S. Pat. No. 5,758,095 to Albaum et al., "Interactive Medication Ordering System," discloses a system and method for ordering and prescribing drugs for a patient. This system includes an improved process for facilitating and automating the process of drug order entry. The user may interact with the system in a variety of ways such as keyboard, mouse, pen-base entry or voice entry. The system includes a database containing medical prescribing and drug information which is both general and patient-specific. The system also permits the user to view current and previously prescribed medications for any patient. The system can alert the user to potentially adverse situations as a result of the prescribed medication based on information in the database.

U.S. Pat. No. 5,299,121 to Brill et al., "Non-Prescription Drug Medication Screening System," discloses a system for use in pharmacies which uses customer inputs to assist the customer with the selection of an appropriate non-prescription medication to relieve symptoms of an illness, injury or the like. The system uses an expert system to perform the selection. The system utilizes a personal computer with a keyboard, monitor and disk drive as input/output devices with appropriate programming for prompting a user to input information which is used by a knowledgebase to determine non-prescription medications which may be purchased by the customer to relieve symptoms of injuries and illnesses included in the knowledgebase.

U.S. Pat. No. 5,594,637 to Eisenberg et al., "System And Method For Assessing Medical Risk," discloses a system and method for assessing the medical risk of a given outcome for a patient comprising obtaining test data from a given patient corresponding to at least one test marker for predicting the medical risk of a given outcome and obtaining at least one variable relating to the given patient and transforming the test data with the variable to produce transformed data for each test markers. A database of transformed data from previously assessed patients is provided, and mean and standard deviation values are determined from the database in accordance with the actual occurrence of the given outcome for previously assessed patients. The transformed data is compared with the mean and standard deviation values to assess the likelihood of the given outcome for the given patient and the database is updated with the actual occurrence for the given patient, whereby the determined mean and standard deviation will be adjusted.

U.S. Pat. No. 6,067,524 to Byerly et al., "Method And System For Automatically Generating Advisory Information For Pharmacy Patients Along With Normally Transmitted Data," discloses a method and system for generating advisory messages to pharmacy patients, including appending patient-specific information to a data record containing normally transmitted information. The data record is transmitted between a third party computer and a pharmacy computer during a pharmacy transaction. The data record transmitted to the pharmacy computer is captured by an advisory computer as the data record is received by the pharmacy computer or after the data record is transmitted to the pharmacy computer, and the patient-specific information is extracted from the captured data record. The advisory computer generates an advisory message based on the extracted patient-specific information, and it transmits the generated advisory message to a pharmacy printer.

U.S. Pat. No. 6,000,828 to Leet, "Method Of Improving Drug Treatment," discloses a computer implemented method and system for improving drug treatment of patients in local communities by providing drug treatment protocols for particular disease states, such as Diagnosis Related Group (DRG) classifications. The protocol contains ranked recommendations for drug treatments of the disease state, and the computer system collects information about the risks and benefits of the drug treatments. The information collected about the treatments is used to modify the rankings of the drug treatments in the protocol.

U.S. Pat. No. 6,219,674 to Classen, "System for creating and managing proprietary product data" discloses systems and methods for creating and using product data to enhance the safety of a medical or non-medical product. The systems receive vast amounts of data regarding adverse events associated with a particular product and analyze the data in light of already known adverse events associated with the product. The system develops at least one proprietary database of newly discovered adverse event information and new uses for the product and may catalog adverse event information for a large number of population subgroups. The system may also be programmed to incorporate the information into intellectual property and contract documents. Manufacturers can include the information in consumer product information that they provide to consumers or, in the case of certain medical products, prescribers of the medical products.

However, none of these references provides a system and method for analyzing the risks of adverse effects resulting from the use of a particular drug, either alone or in combination with other substances including but not limited to hormones, drugs, nutrients, and supplements.

Thus, there remains a need for a more efficient and effective system and method for analyzing the risks of adverse effects resulting from the use of a particular drug, either alone or in combination with other substances including bit not limited to hormones, drugs, nutrients, and supplements. There also remains a need for a more efficient and effective system and method for analyzing the risks of adverse effects resulting from the use of a particular drug on particular segments of the population.

SUMMARY OF INVENTION

The system of the present invention for assessing and analyzing the risks of adverse effects resulting from the use of at least one substance of interest, comprises a selector for identifying at least one substance of interest; a profiler for selecting from multiple profiles related to the safety of the at least one substance of interest, using at least one filter; at least one data mining engine; and an output device for displaying the analytic results from the data mining engine.

The system of the present invention is also a system for assessing and analyzing the risks of adverse effects resulting from the use of at least one drug of interest, comprising: a selector for identifying at least one drug of interest; a profiler for selecting from multiple profiles related to the safety of the at least one drug of interest, using at least one filter; at least one data mining engine; and an output device for displaying the analytic results from the data mining engine.

The method of the present invention for assessing and analyzing the risks of adverse effects resulting from the use of at least one substance of interest comprises identifying the at least one substance of interest; selecting the profile of the at least one substance of interest related to the safety of the at least one substance of interest, using at least one filter; analyzing the risks of adverse effects resulting from the use of the at least one substance of interest using at least one data mining engine; and displaying the results of the analysis of risks of adverse effects resulting from the use of the at least one substance of interest.

The method of the present invention for assessing and analyzing the risks of adverse effects resulting from the use of at least one drug of interest also comprises identifying the at least one drug of interest, as well any other drugs, nutrients, supplements, and other substances; selecting the profile of the at least one drug of interest related to the safety of the at least one drug of interest, using at least one filter; analyzing the risks of adverse effects resulting from the use of the at least one drug of interest using at least one data mining engine; and displaying the results of the analysis of risks of adverse effects resulting from the use of the at least one drug of interest.

Preferably, the system and method of the present invention for assessing and analyzing the risks of adverse effects resulting from the use of a drug of interest, either alone or in combination with other drugs, nutrients, supplements, and other substances comprises at least one data mining engine preferably selected from the group consisting of (1) a proportional analysis engine to assess deviations in a set of the reactions to the drug of interest, (2) a comparator to measure the reactions to the drug of interest against a user-defined backdrop, and (3) a correlator to look for correlated signal characteristics in drug/reaction/demographic information; and an output device whereby a user can receive analytic results from the selector, and the at least one data mining engine.

The present invention also provides a system and method for assessing the relationships between any and all dimensions, in any and all combinations, in assessing and analyzing the risks of adverse effects resulting from the use of one or more particular drugs. For example, the dimensions can be analyzed in combinations of two dimensions, in combinations of three dimensions, and others combinations, as well. As a specific example, the present invention permits a view of a drug reaction (for example, rash) across all drugs. The present invention also permits analysis of the association between outcomes (for example, hospitalization) and other dimensions (for example, age, gender, concomitant drug, reaction, among others).

It will appreciated that such a system and method for assessing and analyzing the risks of adverse effects resulting from the use of one or more particular drugs is advantageous to the various risk assessors who are tasked with making such determinations. Such risk assessors include governmental agents who perform such assessment for regulatory purposes, as well as agents of pharmaceutical manufacturers who are tasked with such assessments.

The present invention, which provides a system and method for assessing and analyzing the risks of adverse effects resulting from the use of one or more particular drugs, offers an enhanced degree of analysis not previously available. This enhanced degree of analysis permits the identification of associations and, thus, potential causal elements regarding adverse effects resulting from the use of one or more particular drugs.

The present invention provides answers to several key questions that are essential to public health. For example, various safety groups, both government and private, are charged with monitoring the post-market behavior of drugs and determining "signals" that indicate a relationship among adverse reactions, demographics, and other elements such as outcomes. Unexpected or previously unrecognized adverse drug effects can take the forms of single reactions, groups of reactions, or increases in a labeled reaction. Such adverse drug effects might be due to the higher exposure to the general population experienced in post-market therapy or such effects can be a reaction that has a demographic (genetic or otherwise) emphasis in an age or gender group.

Further, with efficient and effective analysis of adverse drug effects, pharmaceutical research and development professionals can learn more details of the reaction profiles of drugs and the at-risk populations who may be prescribed those drugs. This information would allow a more effective selection of lead compounds and would produce drugs with less risk of adverse effects.

Thus, the present invention allows for analysis of adverse drug effects with enhanced speed and flexibility. The present invention also offers new insights with regard to adverse drug effects and augments the existing processes of drug development.

Accordingly, it is an object of the present invention to provide a more efficient and effective system and method for analyzing the risks of adverse effects resulting from the use of a drug, either alone or in combination with other drugs, nutrients, supplements, and other substances.

It is an object of the present invention to provide a more efficient and effective system and method for analyzing the risks of adverse effects resulting from the use of a drug.

It is further an object of the present invention to provide a more efficient and effective system and method for analyzing the risks of adverse effects resulting from the use of a drug in combination with another substance.

Yet another object of the present invention is to provide a more efficient and effective system and method for analyzing the risks of adverse effects resulting from the use of a drug in combination with another substance, wherein the substance is a nutrient, vitamin, hormone, or drug.

An advantage of the present invention is that potential adverse effects to the health of a human or animal may be predicted and avoided.

Yet another object of the present invention is to provide a more efficient and effective system and method useful for analyzing the risks of adverse effects resulting from the use of a drug, alone or in combination with another substance, wherein the substance is a nutrient, vitamin, hormone, or drug, further wherein the system and method can be used by providers of medical or veterinary care services.

Another object of the present invention is to provide a more efficient and effective system and method useful for analyzing the risks of adverse effects resulting from the use of a drug, alone or in combination with another substance, wherein the substance is a nutrient, vitamin, hormone, or drug, further wherein the system and method can be used by consumers of medical care services.

A greater understanding of the present invention and its concomitant advantages will be obtained by referring to the following figures and detailed description provided below.

BRIEF DESCRIPTION OF DRAWINGS

FIG. 4 is a representation of a filter selection page of the present invention;

FIG. 5 is a representation of a selector page of the present invention;

FIG. 6 is an illustration of an exemplary pedigree screen of the present invention;

FIG. 8 is a representation of a concomitant drugs table in the profiler component of the present invention;

FIG. 9 is a depiction of a demographics table in the profiler component of the present invention;

FIG. 11 is a representation of an outcomes table in the profiler component of the present invention;

FIG. 12 is a depiction of a reaction filter screen of the present invention;

FIG. 13 is an illustration of a correlation results screen of the present invention;

FIG. 14 is a representation of a correlation details screen of the present invention;

FIG. 15 is a depiction of a case details screen of the present invention;

FIG. 17 is an illustration of a proportional analysis selection screen of the present invention;

FIG. 20 is an illustration of a comparator screen of the present invention; and

FIG. 21 is a representation of a case list of the present invention.

DETAILED DESCRIPTION

The present invention provides a system and method for assessing and analyzing the risks of adverse effects resulting from the use of one or more particular drugs, either alone or in combination with other drugs, nutrients, supplements, vitamins, foods, beverages, and other substances.

The primary components of a preferred embodiment of the present system and method for analysis of adverse drug effects are a combination of the following: one or more integrated databases; a selector for selecting at least one drug for analysis (based on the generic, brand names or therapeutic category); a profiler for displaying statistics that describe behavior for the drug in multiple dimensions; a series of at least two filters and the means to control the at least two filters individually and in combination; at least one of three or more data mining engines selected from the group of a correlator, a proportional analysis engine, and a comparator; and a graphical user interface for displaying the results of the analysis.

For purposes of the present invention, a substance shall be understood to include one or more elements of the set of drugs, foodstuffs, beverages, nutrients, vitamins, toxins, chemicals, hormones, and supplements.

Figure 1:
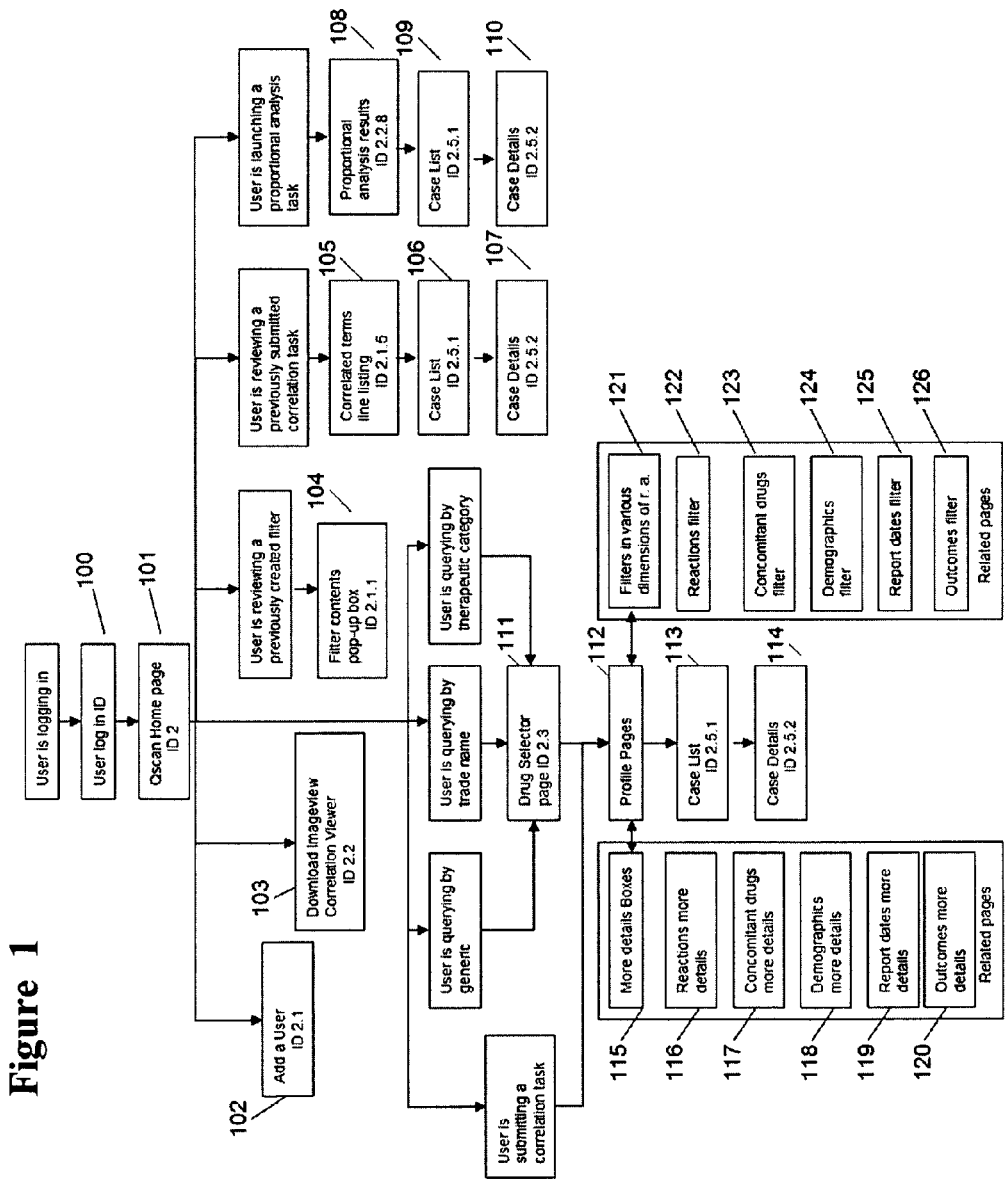
FIG. 1 is chart indicating the page flow of the present invention.

A preferred page flow of the present invention is indicated in FIG. 1. Box 100 represents a user login window. If the user successfully logs in and is authenticated, then the user is then placed in the home page 101 of the present invention. From the home page 101, the user can add a user at the Add a User Box 102; download an data image at the ImageView Correlation Viewer Box 103; review a previously created filter at the Filter Contents Pop-up Box 104; review a previously submitted correlation task at the Correlated Terms Line Listing Box 105; launch a proportional analysis task at the Proportional Analysis Results Page Box 108; or query the system with regard to a drug at Drug Selector Page Box 111. It will be appreciated that the user can query regarding a drug by generic name, trade name, or therapeutic category.

Preferably, if the user is reviewing a previously submitted correlation task at the Correlated Terms Line Listing Box 105, then the present invention permits the user to access the case list at the Case List Box 106 and, further, permits the user to drill down on individual elements in the case list and obtain case details at the Case Details Box 107.

Preferably, if the user is launching a proportional analysis task at the Proportional Analysis Results Page Box 108, then the present invention permits the user to access the case list at the Case List Box 109 and, further, permits the user to drill down on individual elements in the case list and obtain case details at the Case Details Box 110.

Preferably, if the user is querying the system with regard to a drug at Drug Selector Page Box 111, then the present invention permits the user to access the drug profile at the Profile Page Box 112, further, permits the user to access the case list at the Case List Box 113 and, still further, permits the user to drill down on individual elements in the case list and obtain case details at the Case Details Box 114.

From the Profile page Box 112, the user preferably can either access more details regarding the various dimensions of the risk assessment at the More Details Box 115 or filter in various dimensions of the risk assessment at the Filter in Various Dimensions Box 121.

If the user has chosen to access more details, then the user is preferably presented with multiple dimensions of the risk assessment from which to access more information. Preferred dimensions of risk assessment include, but are not limited to, Reactions More Details Box 116, Concomitant Drugs More Details Box 117, Demographics More Details Box 118, Report Dates More Details Box 119, and Outcomes More Details Box 120.

Preferably, if the user has chosen to filter in various dimensions of risk assessment, then the user is preferably presented with multiple filters for the dimensions of the risk assessment. Preferred filters of dimensions of risk assessment include, but are not limited to, Reactions Filters Box 122, Concomitant Drugs Filters Box 123, Demographics Filters Box 124, Report Dates Filters Box 125, and Outcomes Filters Box 126.

Figure 2:
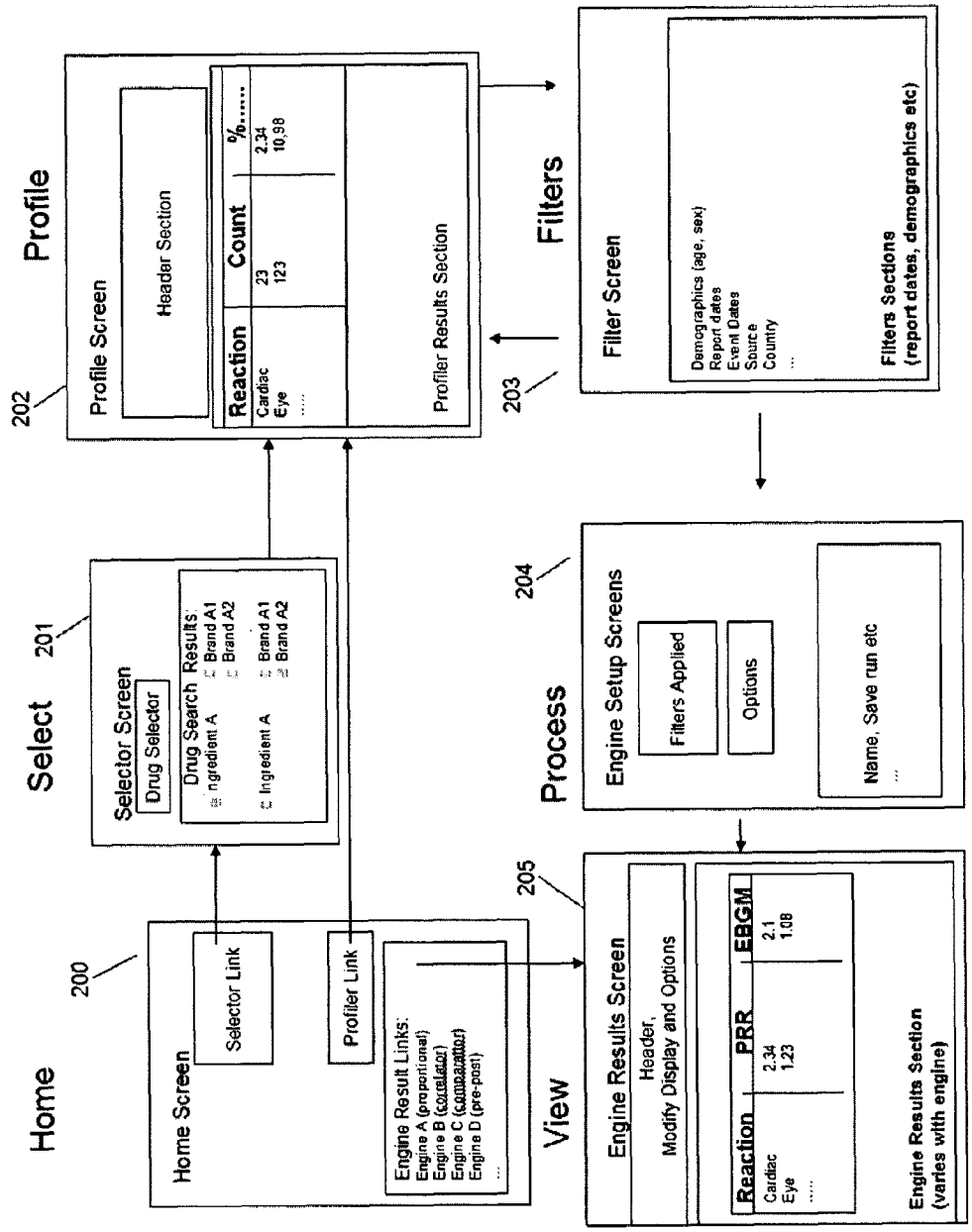
FIG. 2 is an overview of the present invention.

The preferred components of the present invention are illustrated in FIG. 2, which provides an overview of the system and method of the present invention. The user preferably accesses the system of the present invention by means of Home Page 200. From Home Page 200 the user can proceed to the Selector 201, where the user can select a drug for analysis. Having selected the drug of interest, the user can then preferably proceed to the Profiler 202, which preferably displays statistics that describe the behavior of the drug of interest. From the Profiler 202 the user can then preferably proceed to employ one or more Filters 203, which permit recalculation of the statistics by selecting among the available variables. Once a set of cases is determined, for example, by the use of one or more filters, the cases can then preferably be submitted to at least one of three or more Data Mining Engines 204. The output from the data mining engines is then preferably displayed in a Viewer 205, which can present the data in a variety of formats, including, but not limited to a sortable table, a sortable line listing, and a radar screen, thus, allowing rapid identification of signals and providing the user the ability to drill down to individual case details.

Alternatively, in another preferred embodiment, from Home Page 200 the user can choose a profile from the Profiler 202, apply one or more Filters 203, process the set of cases using the Data Mining Engines 204 and display the results with the Viewer 205.

Preferably, the present invention operates on at least one of two integrated databases: an external public database characterized by breadth of data across all drugs and a database containing internal data of an organization or an individual characterized by increased detail with regard to one or more specific groups of drugs. It will be appreciated that a database containing the internal data of an individual can refer to a number of different situations, including but not limited to the biological/medical/genetic/drug sensitivity of an individual.

In both cases, the source and purpose of the data may vary, including post-marketing surveillance, clinical trial data, health care system data, research databases, and literature, among others.

The public database preferably is at least one database selected from either a combination of one or more of the FDA's Spontaneous Reporting System (SRS)(after to November 1997)) and the FDA's Adverse Event Reporting System (AERS)(after to November 1997)), the World Health Organization adverse event database, or other country-specific regulatory or epidemiological databases, such as the UK Advert system and the General Practice Research Database (GPRD). These public databases are updated regularly as they release new case data. In a related invention, which is a particularly preferred embodiment of the present invention, the present system and method for analyzing adverse drug effects relies upon a derivative of these public databases that has cleaned, parsed in to a relational database, and mapped to known dictionaries, and standardized for efficient searching and query defining. This preferred derivative database has over 2 million cases representing 30 years of adverse events as reported to regulatory authorities. Additionally, the derivative database links the adverse event (AE) case data to Medical Dictionary for Regulatory Activities (MedDRA), Coding Symbols for a Thesaurus of Adverse Reaction Terms (COSTART), and World Health Organization (WHO) Adverse Drug Reaction Terminology (WHOART), among others for reactions, and the National Drug Code Directory (NCDC), Orange Book or WHO Drug dictionaries for drugs. The invention includes the facility to substitute and manage standard dictionaries, both public and private, for all dimensions.

In a preferred embodiment, the present system and method also operate on a database containing internal data of an organization. For example, such an internal database could be the proprietary database of a pharmaceutical company or the contemporaneous database of a clinical investigator during the course of clinical trials upon a drug.

It will be appreciated that one preferred embodiment of the present invention utilizes a log-on screen. In one preferred embodiment, access to the present invention is provided by means of the Web. In another preferred embodiment, access to the invention is provided by means of a client/server interface. The present system and method preferably supports all browsers including Netscape and Internet Explorer for access. In a particularly preferred embodiment, different URLs are used for the public database and for the internal database. This allows operating in two databases concurrently if two instances of the Web browser are opened. It also allows virtually unlimited simultaneous processes, and simultaneous processing at various locations.

The use of multiple sessions also enable a range of comparisons, in each and every dimension. The "differencing engine" or comparator provides immediate information on similarities and differences.

In another preferred embodiment of the present invention, a home screen is used to launch searches, and review results of the analytical engines and prior work. For example, from the home screen a user can (1) select a drug to study by either name or by therapeutic category, (2) recall a previously saved filter (that was created, named and saved previously, (3) review previously submitted analyses, or (4) invoke certain data mining engines directly. An exemplary version of a home page of the present invention is provided in FIG. 3. From this home screen, the user can use field 301 to select a drug to study by generic name, trade name, or therapeutic category.

The user can also use field 302 to recall a previously saved query (called a filter). Further, the user can use field 303 to recall previously submitted analyses. Additionally, the user can use field 304 to invoke the proportional analysis engine.

The home page is preferably the user's command center for analysis. The home page is preferably always accessible from any other screen.

Preferably, the home screen has four areas. The first area is a link to the selector, thus, allowing a user to easily reach the drug selection screen through any level of detail on a drug. The second is a filter area. The user can view and apply previously saved filters. The third section is the data mining engine section which allows a user to invoke one or more of the data mining engines. The fourth area permits the user to review previously generated analyses.

With regard to the selection of a drug, this feature allows a user to select at least one drug to study and to search for information on that at least one drug by using either its generic name, its trade name, its therapeutic category, or its chemical name. In addition, the invention provides the ability to develop specific other valuable taxonomies, such as a "super generic" including all salts of a drug, or a sub-brand, for example distinguishing between a once a day version of a drug from a once a week version of the drug.

Concerning selecting a previously saved query, this feature (referred to as a filter) is a preferred paradigm to reduce the routine of inputting a previously employed and saved query. By establishing parameters for searching, a user does not need to define ad hoc queries. Knowledge of the pharmacovigilance domain is used to present users with filter/query-building interfaces that are more in line with the thought processes and paradigms employed by such users. A user can preserve the set of parameters of a query (a filter) each time he/she refines a profile, and further, a user can employ a filter he/she has developed in a previous search the next time he/she wishes to view the same or an updated set of cases.

It will be appreciated that one aspect of the present invention is that the combination of profiles and filters allows a user to employ continuous drill-down and hypothesis testing in real time so as to assess and analyze risk. It will further be appreciated that the present invention, by permitting a user to quickly switch on and off the elements of a filter using context-sensitive tables provides an enhanced system and method for assessing and analyzing risk in real time. Examples of the use of such "quick" filters are selecting and/or deselecting the "Designated Medical Events" as defined by the FDA; selecting and/or deselecting labeled adverse effects; selecting and/or deselecting groups of reactions that represent a syndrome.

For example, FIG. 4 provides a representation of a preferred filter screen. Various preferred fields of a filter screen are presented, including, but not limited to, Reactions (field 400), Concomitant Drugs (field 401), Demographics (field 402), Report Dates (field 403), and Outcomes (field 404).

In invoking a saved filter, a user is offered the option of viewing or applying (querying with) a saved filter, and a pull-down menu allows a user to select one of the filters previously created and saved. Pushing the "View" button allows a review of the specific details of the filter. In the example provided, a user had created and saved a filter he/she had labeled "Filter 2" for a search on Candesartan Cilexetil. The search results show the drug's Reactions, including its MedDRA Hierarchy Group (System-Organ-Class (SOCs), etc.), and a pull-down menu showing the specific reactions (ear and labyrinth disorders, for example) included in the filter.

Case sets, as well as drug sets, can be created, named, and saved similar to filters. Because these case sets generate a list rather than a logic description, viewing and changing are performed with a list manager. Filters, drug sets, and case sets can all be combined or merged to provide a rich set of functions, and great flexibility.

The preferred parameters of a filter include reactions (listed as "included" or "off"); concomitant drugs (listed or "off"); demographics (listed as per previously set brackets or "off"); report dates (listed or "off"); and outcomes (listed or "off"). If a user wishes to apply this saved filter as his/her current query, he/she would click on the "Apply" button. At this point, a user would be taken to the profile screens for that drug and that set of filters.

The present invention allows for flexible addition of dimensions. For example, if genotype or racial background were added as a dimension, the present invention would display, control and analyze this dimension, along with the other dimensions of issue.

Figure 3:
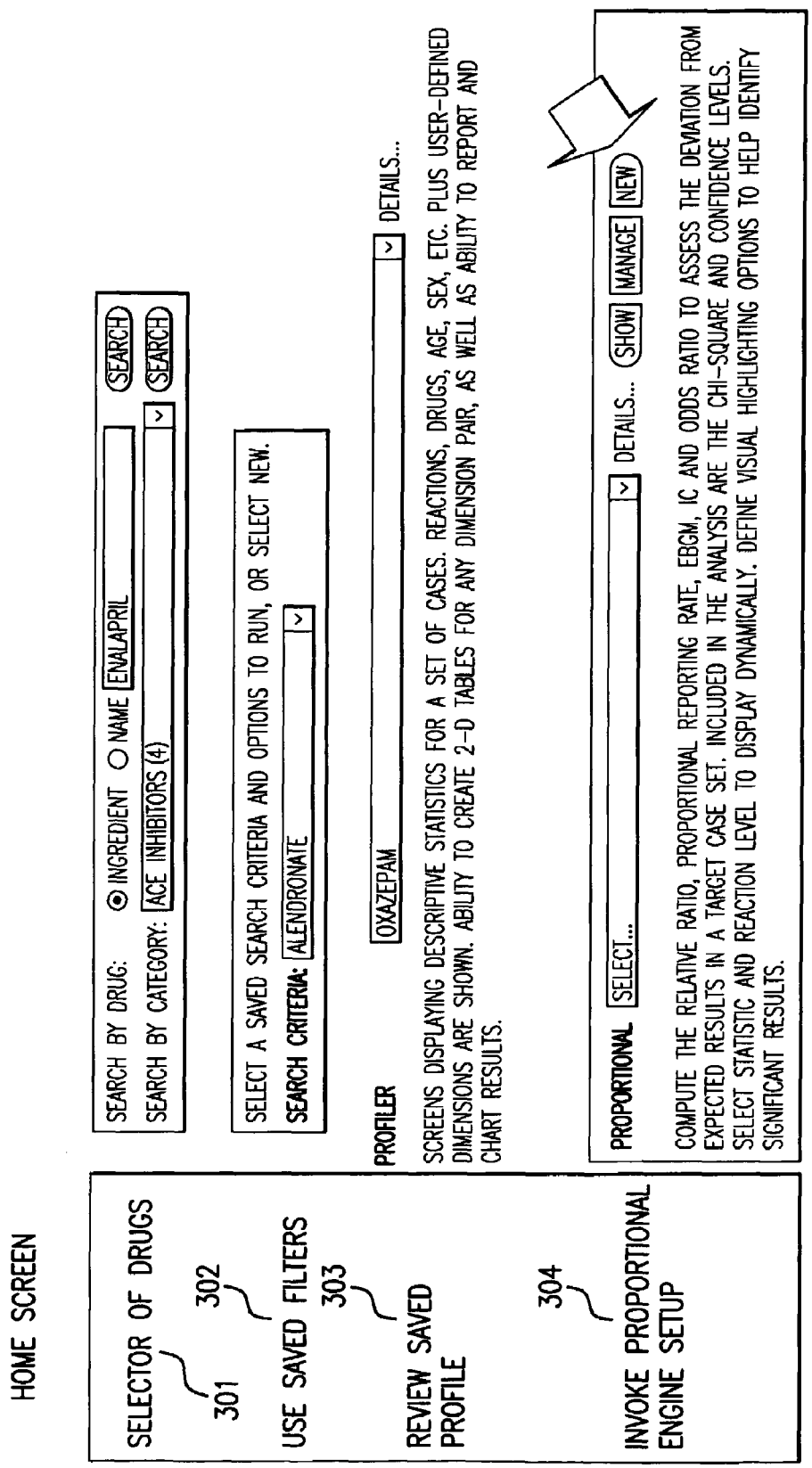
FIG. 3 is a depiction of a home page of the present invention.

With regard to the review of the previous analysis aspect of the present invention, this section of the home page provides information on previous analyses a user has run using the correlator engine of the present invention. As illustrated in FIG. 3, the correlator engine notices provide information on analyses that have been previously completed including date and time, task number, and generic drug. Each listing ends with a hyperlink that a user can employ to view the results of the search. A "delete" function is preferably provided to manage this list.

Concerning the proportional analyzer aspect of the present invention, this component looks for large or small deviations in the reactions counts for a set of drugs, i.e., comparing drugs to those in their own therapeutic category or to all drugs. With a preferred embodiment of the present invention, a user has an option to compute for a therapeutic category using a pull-down menu. A user also has an option of selecting Bayesian filtering. Bayesian filtering employs a statistical cut-off threshold to reduce the affect of rows or columns with a very low number of cases. That is, drugs or reactions accounting for less than a certain percent of cases or fewer than a set number will be deleted from the matrix (and so noted on the results screen).

A user preferably has two options in running this analysis: (1) he/she can compute information for each drug's reactions in comparison with all of the drugs in the system or (2) a user can run an analysis by comparing the selected drug's reactions only with those of other drugs in the same therapeutic category. Results are preferably presented concurrently on a separate screen.

An additional preferred aspect of this home page is a comparator, which is available when a user is accessing optionally provided clinical trial data from a drug label, or from the clinical trial data of an internal database. The comparator compares potential and actual adverse effects of drugs in the pre- and post-market environments.

The preferred home page of the present invention also provides a user with the options to add a user, manage preferences, manage the group of inserts, and to log out, among others.

If a user has selected a query at the Home page, he/she will initiate a query for a drug using the drug's generic name, its trade name, its therapeutic category, its chemical name, or other custom-defined categories. The search invokes the selector page of the present invention. A user selects a drug by clicking on the generic drug link which then takes a user to the profile and general statistics regarding the selected drug. A user starts his/her search on the home screen, and then continues it on the selector page, by entering or selecting the category of drug he/she wants to search: the generic name, the trade name, the therapeutic category or the custom-defined categories. The therapeutic category field preferably has a pull-down menu to help identify and select the desired field.

An exemplary Query Screen page is illustrated in FIG. 5, where a user has decided to search the therapeutic category of angiotensin converting enzyme (ACE) inhibitors, as defined by the drug dictionaries. (Note: In this case the FDA taxonomy places certain drugs known as ATII drugs in the ACE category.) Here, the user has chosen not to use the generic name field 500 or the trade name field 501, but rather has chosen the therapeutic category field 503. The present system returns with the hits corresponding to the selected therapeutic category and are displayed in the query screen. In this example, 4 drugs matching the search criteria were found in the "ACE Inhibitors" category. The drugs are listed in alphabetical order by their generic name. For each generic drug on the list, all trade names and all relevant therapeutic categories are presented in pull-down menus. Optionally, custom-defined categories can also be shown. The search results also allow access to the drug's "pedigree," or lexical mapping information, indicated by a question mark link.

Preferably, a user can stop browsing drugs and go directly to the profile by selecting and applying a previously stored filter.

With regard to the pedigree function, if a user selects the pedigree icon for the selected drug (the question mark in this example), a user is presented with the drug's pedigree, which shows the way the drug has been mapped in a drug dictionary and thesaurus.

An exemplary pedigree screen is presented in FIG. 6. This exemplary pedigree screen provides a number of preferred fields indicating the cataloging of the data in the system of the present invention. Preferred fields include, but are not limited to, Map To (field 600), Verbatim (field 601), Source (field 602), Incidents (field 603), Case Count (field 604), QEDRx Processing (field 605), Cross-Reference (field 606), and First/Last Reported Reactions (field 607). The data pedigree search not only shows how the drug is catalogued in the present invention, it also shows the drug's mapping to known dictionaries. These data are displayed in a tabular form, and indicate the logical route from verbatim terms to the "map to" terms used to search the database. This function informs the user of specific ranges, types of corruption and number of each type of corruption in the data that have been corrected.

For example, a preferred pedigree screen of the present invention provides categories including Map to, Verbatim, Cross-Reference, Incidents, Case Counts, QEDRx Processing, First/Last Reported Reactions, and Source. The Map to category shows how the verbatim name was mapped to a generic or trade name. The Verbatim category shows the verbatim name the drug was found under in the database. This can be any form of the name under which this drug was found in the. FDA database, and includes misspellings, variations, etc. The Cross-reference category indicates which data source contains this verbatim, the SRS database or the AERS database, etc. The Incidents category indicates the number of times this verbatim appears in the database. The QEDRX Processing category refers to the "cleanup" performed on the data. The specific processing steps are defined in a key. The Source category indicates which reference data source was used to map this verbatim to a generic.

The key explains the types of processing that the system and method of the present invention performs to standardize drug names and to improve the quality of the reported data.

The present invention preferably performs five types of processing: spelling correction (corrects misspelled drug names and standardizes variations in drug names), noise words (words like, for example, "tablets" "Prozac tablets" does not offer further information about the drug itself; it simply provides information on how the drug was administered), combo words (alphanumerics like "20 mg.," for example, which are redundant because already in the database), numerics (the "20" in 20 mg. In this case, 20 is a numeric and "mg" is a noise word), marks (extraneous typographic symbols, such as brackets, dashes, and so forth). Additional aspects of this feature of the present invention are provided in U.S. Pat. No. 6,778,994, entitled Pharmacovigilance Database, which is incorporated herein by reference.

The profiler aspect of the present invention permits a user to navigate various dimensions of the selected drug's safety profile and view cases, concomitant drugs, reactions, demographics, outcomes, and time intervals using specified filters. Once a user is satisfied with the cases profiled, the set of cases satisfying the filter criteria can then be submitted to the various data mining engines, including the Correlator Engine (CE), Proportioning Engine (PE) and Differencing Engine (DE). Each data mining engine is provided with a set-up and a verification step (by means of a page set of input parameters). For example, the CE may further weight the different dimensions.

It will also be appreciated that the profiler of this invention allows for continuous adjustment and addition to the dimensions. For example, a preferred embodiment includes "Repeat Source". Others may contain laboratory results. The invention permits expanding and contracting both the profiler and the at least two filters as the data changes.

As noted above, in the selector component of the present invention, each of the drugs in the generic name category is preferably presented in a format that indicates a hyperlink. Clicking on a generic drug (in the previous example Candesartan Cilexetil), the multi-dimension profile screen is invoked by clicking on a generic drug (in the previous example Candesartan Cilexetil).

The idea of profiling a drug is complex, because of the multiple dimensions. The invention's profiler separates presenting data on the selected drug into several different categories and preferably "billboards" the top ten for immediate visibility. It will be appreciated that the user can specify any number for "billboarding." At the top of the screen are the generic name of the drug (preferably with a hyperlink to its pedigree), all the trade names associated with the drug, and all of the therapeutic categories to which it belongs.

The profile feature of the present invention is used to display statistics that describe the effects of the drug in multiple dimensions. Each set of data is preferably presented in a separate table, headed by an index tab. The preferred data sets include, but are not limited to: (1) Reactions; (2) Concomitant Drugs; (3) Demographics; (4) Report Dates (for example, dates logged by FDA as report dates for SRS and AERS); and (5) Outcomes.

For each dimension there are key actions: all allow filtering and delving for more details. The filter action allows a user to set and activate filters for that dimension. The "More Details" action brings up all the values that have appeared only in the top 10 billboard style on the main page.

For certain dimensions, for example reactions, the hierarchy of the dimension can be selected to change the billboard and detailed views. In the case of reactions, MedDRA contains a five level hierarchy. Other dictionaries use two to four levels. The present invention accommodates the full range of hierarchies.

Preferably, the profiler feature of the present invention allows grouping concomitant drugs by therapeutic category, chemical class, or other custom-defined class.

With regard to the Reactions dimension, the profiler component of the present invention preferably shows reactions to the drug that is being queried. This dimension refers to suspected adverse reactions to the selected drug that were reported. A suitable reactions table is provided in FIG. 7. In this figure, to the right of the Reactions tab is a pull-down menu labeled "View" 700, followed by a filter hyperlink 701. By utilizing the pull down menu, a user can choose among multiple different levels of MedDRA. Of these multiple different levels of MedDRA, four are particularly preferred. These are System, Organ, Class (SOC), High Level Group Term (HGLT), High Level Term (HLT), and Preferred Term (PT).

Figure 7:
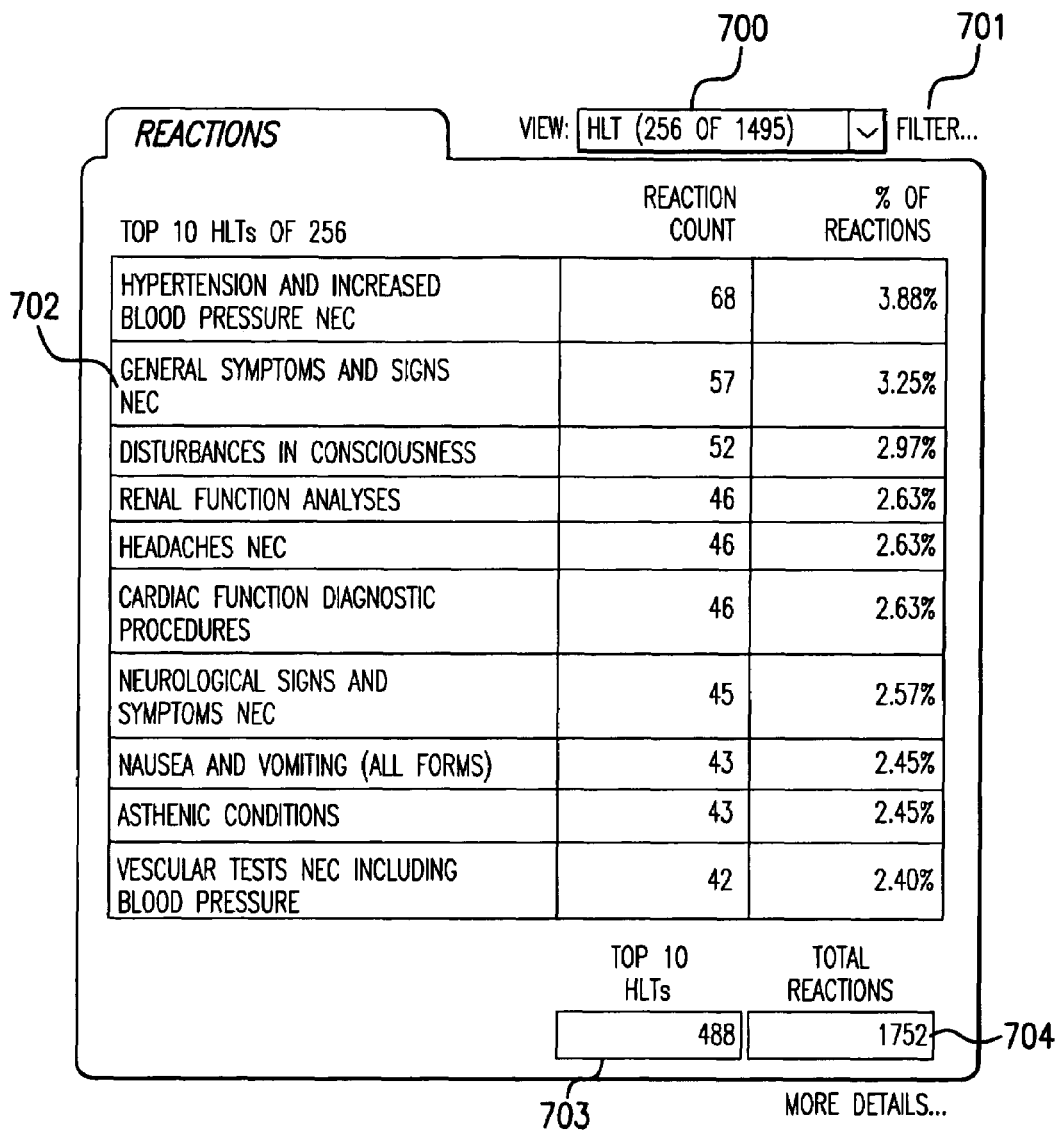
FIG. 7 is a depiction of an exemplary reactions table in the profiler component of the present invention.

In FIG. 7, a user has chosen the HLT option. The window in the pull-down menu indicates that there are 256 HLTs out of the total of 1495 HLTs in the current version of MedDRA. The Reactions Table 702 shows the Top 10 HLTs of the 256. In this case, the reactions include hypertension, disturbances in consciousness, and so forth. For each of the reactions, the table presents the Reaction Count (the number of times this reaction was listed in the database) and the percentage of reactions that this number constituted in the set of reactions for this drug, based on incidents of reactions (not cases).

At the bottom of the Reaction Count and % of Reactions columns are numbers showing the number of incidents of the reactions at the Top 10 HLTs (488) and the Total Reactions across all of the 256 HLTs (in this case, 1752), 703 and 704, respectively.

The ability to browse statistics, up and down a hierarchy, and within real time, is important to keeping risk assessment hypothesis setting and testing within a short period of time. The invention provides extensive associative tables and reverse indexing to enable such rapid analysis.

A hyperlink offering more details concurrently follows the Reactions table, and brings up a separate page with all details of this dimension.

It will be appreciated that since Reactions, Concomitant Drugs, and Outcomes are summarized at the event level, the resultant collection of cases will be different if more than one event is associated with a single case. For example, if two reactions are recorded in a single case, and both of those reactions parent to the same MedDRA SOC, then they will account for two events, and yet would yield only a single case in the case listing.

In a preferred embodiment of the present invention, case level percentages and percentage relative to drug exposure are also available in the profiler component of the present invention. With regard to the Concomitant Drugs dimension of the profiler of the present invention, this dimension describes drugs that were also prescribed in the cases in which the target drug was found. A suitable example of a Concomitant Drugs table is provided in FIG. 8.

In this figure, the Concomitant Drugs Table 800 lists the top 10 drugs in the concomitant category. In this example, hydrochlorothiazide, aspirin, and furosemide were among the drugs found in combination with Candesartan Cilexetil in the adverse reactions reported to the FDA.

The table divides the cases of concomitant drugs into two groups: Suspect and Non-suspect (fields 801 and 802, respectively). When an adverse reaction report is filed, certain drugs in the case may be indicated as suspect. When considering concomitant drugs, these drugs will be either suspect or not in the cases relating to the queried drug (in this case, Candesartan Cilexetil). Thus, in this example there are four cases to consider, suspect and non-suspect for the queried drug, and suspect and non-suspect for the concomitant drug.

In the example, Hydrochlorothiazide is the drug found to be most frequently interacting with Candesartan Cilexetil. The total number of incidents (45) is broken out into the Suspect and Non-suspect categories, and the total is also displayed as a percentage of cases that mention this concomitant drug (it is assumed a drug is only mentioned once per case), in this case 10.79% of the total number of cases involving Candesartan Cilexetil. The remaining Top 10 concomitant drugs are listed in order of descending frequency.

Because it is difficult to predict the number of drugs that are reported, the drug detail section provides browser paging and sorting. Paging and sorting are techniques of the invention used to "bubble to the top" the significantly hypothesized items.

Concerning the Demographics dimension of the profiler component, this table provides demographic information about the population included in the query. An appropriate demographic table in the profiler of the present invention is provided in FIG. 9. Preferably five age groups, ranging from below 16 to above 75, are included in field 900. The data is also preferably broken out by gender (field 901). The category totals and percentages are also provided. The detailed listing gives the statistics by single age rather than by generational grouping.

Figure 10:
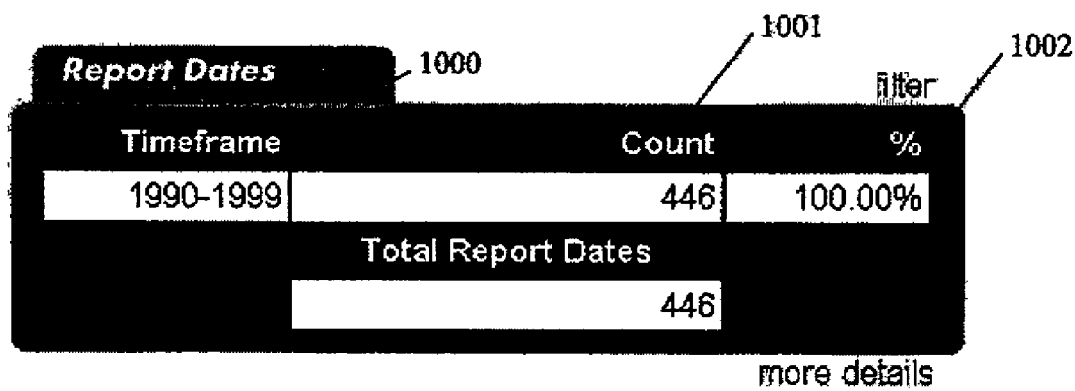
FIG. 10 is an illustration of a report dates table in the profiler component of the present invention.

Regarding the Report Dates dimension of the profiler component, report dates for the incidents included in the selected drug query are presented. A suitable report dates table is presented in FIG. 10. In the example, the time interval (field 1000) is the decade 1990-1999 and shows the number of reports in each of those years for the drug Candesartan Cilexetil.

The time interval of the incidents included in this query is presented in this table. In the example, the time interval is 1990-1999 and shows the total number of reports for that period (field 1001)(446) and the percentage (field 1002)(in this case, 100.00%) of reports for the drug Candesartan Cilexetil that fall within that time interval. By selecting the more details link, a user can obtain the breakdown of the reports by individual years.

In the Outcomes dimension of the profiler of the present system and method, case outcomes are listed. An appropriate outcomes table is presented in FIG. 11. Preferred categories include serious outcomes such as congenital anomaly, death, and disability, as well as other outcomes. Serious outcomes are preferably presented in red, while less- or non-serious outcomes are in black. The Outcomes Table provides a table of outcomes (field 1100), a count (field 1101) and percentages of the outcomes (field 1102) in each category, as well as totals of serious and non-serious outcomes.

The filtering feature of the present invention is a paradigm that reduces the routine of constructing ad hoc queries. This filtering feature is context-sensitive and relieves a user of the burden of repeatedly defining the parameters of the queries. Filtering allows a user to formulate queries in a way more consistent with paradigms used by medical professionals, selecting among the active cases and using standard dictionaries such as MedDRA and National Drug Code Directory. This filtering features preferably allows a user to apply and view filters individually, set filters as a group and apply globally, or save and apply filters at a later time.

Data is compiled by the filters selected for each analysis. In the above example, filters were established for the reaction query. One of the screens in the profiler component was the reactions dimension, providing the Top 10 SOCs for the drug Candesartan Cilexetil. At the top of the table was a pull-down menu with "View" selected, also provided with a filter hyperlink.

Each of the data sets in the Profiler (Reactions, Concomitant Drugs, Demographics, Report Dates, and Outcomes) provides a user with the opportunity to establish filter parameters in any order. In a preferred implementation, the invention tabs the individual filters for convenience, and allows merging with other filters.

An exemplary filter applied as to reactions is provided in FIG. 12. This figure provides the list of Reaction Filters available for profiling. The filter is based on the MedDRA hierarchy and begins at the SOC level.

The mechanics for working with filters is common to all dimensions. A user may click on any or all of the reactions they would like to have included in the filtered reaction profile.

In the example of Reaction filtering, clicking on an SOC brings up the HLGTs for that SOC and allows selection at that level.

In a preferred embodiment filtering can be done at all levels.

It will be appreciated that for the more complex filters, such as the reaction filter, a range of user friendly aids is provided. For displayed MedDRA leads, preferably a tree is used. When it is collapsed, an open box preferably means no selections lower in the hierarchy have been identified, a check means all lower selections in the hierarchy have been identified, and a new query box is used to indicate unchecked box(es) somewhere below in the hierarchy.

Another preferred feature of the present invention is content-based pre-filters. To make it easier to switch-off indication-related adverse drug reactions, an "indications-related" button is preferably provided in the selection. For labeled adverse effects, of which there could be hundreds, the invention preferably provides tables (in this case with data from drug labels) to switch off all of the labeled reactions. This quickly focuses the user's attention on "unexpected" reactions.

Preferably on the profiler component, the present invention monitors the contents of each filter as it is built. At any point, the filter can be saved as an entirely new filter or by overwriting an old one, or changing and saving an incremental filter. This permits fine tuning of hypotheses regarding adverse drug reactions.

The filter for the concomitant drugs dimension allows selecting or deselecting any and each of the concomitant drugs reported in the profiled set of cases. Similar to reaction filtering, the concomitant drug dimension filter preferably provides a context selector (for example, to switch out a whole therapeutic category).

The demographics filter allows selections of generational or individual age brackets, and male/female selections as well. Generational filters are preferably user definable.

The report dates dimension allows selection by bracketed years. In addition, in another embodiment of the invention, the report dates filter incorporate a link to a drug's birth date and allow filtering by "first six months," "first two years," etc. A table of drug birth dates relieves the user of the need to separately enter those dates.

The Outcome filter allows individual outcome selection, or by serious/non-serious grouping. For internal database adverse events, if a custom seriousness set is defined, this dimension will be user definable.

The analysis provided by the system and method of the present invention finds "signals" such as anomalies in a random population, a change against a known background, or a coherent target in a noise background. This is accomplished by at least one of three or more data mining engines: the proportional analysis engine (PE), the comparator (differencing engine or DE), and the correlator. In a preferred embodiment, the proportional analysis engine can be invoked from the home screen, as can be the comparator, for selected data. The correlator is invoked after filtering cases from the profile page.

The correlator looks for the association of characteristics in literally millions of pieces of drug/reaction/demographic information concurrently.

Too often in risk assessment, important correlations are hidden by surrounding background "noise" that obscures connections among data elements. Using a multidimensional vector analysis, the correlator measures the degree of association among pairs of values (for example, a drug and a reaction, an age and an outcome, etc.). The correlation algorithm is user selectable and definable. The preferred version uses a Pearson product-moment correlation known conventionally as "$R^2$". Other algorithms can also be used. The invention preferably applies the correlation after filtering, greatly enhancing the signal and reducing noise.

As a preferred example, the profiler screen can provide a number of hyperlinks choices, including "Apply Filter" and "Compute Correlations. " selecting "Compute Correlations," a user initiates the correlator engine, using the active set of cases, based on the filter in use. While the processing is being carried out, a user is preferably returned to the home screen, where a message alerts a user that the correlation is being executed. Once the analysis is completed, a user is notified that the correlation has been completed and providing a user with the option to view the correlation results.

FIG. 13 provides an exemplary screen presenting the results of a correlated search. The line listing of correlated terms (which may be several screens in length) consists of the top 200 (this cut-off number can be any number that the user specifies and is selectable and sortable) sets of correlated terms for a user's analysis on the requested drug. The data compares the correlations between "Term 1 " and "Term 2." For each pair of terms, the screen preferably shows its relative rank (field 1303); score (field 1304)(the term-pair's correlative value relative to other term-pairs, for example, "Female" and "Candesartan" are more "associated" than any other pair of terms, for example, in the set of cases containing "Female" and "Candesartan," were relatively highly correlated); the identity of the first term (field 1300) and the category to which it belongs (field 1305); and the identity of the second term (field 1301) and the category to which it belongs (field 1306).

Although the product moment correlation has been employed in a number of areas, it has typically been used for numerical data. The invention sends the correlator a vector comprising almost entirely of categorical terms, a new and previously unexplored use of the Pearson $R^2$. The present invention's structural database, its ability to keep a consistent vocabulary (to name categories of a categorical variable) and its ability to provide sufficiently cleaned data regarding adverse drug reactions make the correlation meaningful. The present invention's ability to sort results, compare significance and handle thousands of cases was not available in the prior art. Since the correlator calculates association strength for both known factors (for example, age and gender) and rare reactions (for example, adverse drug reactions (ADR's)), this invention can identify meaningful relationships not otherwise easily observed.

In addition to viewing the table listing online, a user may also preferably select to review the results using a "radar-screen" correlation viewer. On the correlation screen, after the "Below are the top 200 correlated terms for your analysis . . . ," there is preferably a hyperlink that provides the option of viewing the results with the correlation viewer. In addition to viewing with the correlation viewer, a user is also preferably presented with options to save the file.

Two other information screens preferably provide additional information provided by the correlation engine. From the correlated terms screen, a user is preferably presented with hyperlinks comprising all of the numbers in the Rank column. A significance (to a user-selectable "P" value) is also preferably provided. These hyperlinks provide a link to individual case lists. An exemplary correlation details screen is provided in FIG. 14.

The Correlation Details screen of FIG. 14 provides the data for each of the cases included in that pair of correlated terms. For example, if the term pair in the Correlated Terms Screen was "Female" and "Candesartan Cilexetil," this screen provides the pertinent information for all of the cases where those two terms were paired. In this example, there were 18 cases where renal function analyses were correlated with Candesartan Cilexetil. For each case, preferably the following information is provided: the case ID (field 1401); the gender of the patient (field 1402); the Manufacturer's Control Code (field 1403); the FDA Report Receipt Date (field 1404); the patient's age (field 1405); the other drugs the patient was taking at the time of the incident(s)(field 1406); the patient's reaction(s) to the medications (field 1407); and the outcome (field 1408). By selecting these cases, the user can then profile the set of cases.

Additionally, to learn the details of a specific case, a user preferably can click on the case ID number of any case on the Correlation Details screen. The resultant information is preferably presented in a case details screen. An suitable case details screen is presented in FIG. 15.

The Case Details screen of FIG. 15 provides detailed information on each specific case. In addition to standard information such as the patient's case ID (field 1501), gender (field 1502), and age (field 1503), it preferably includes Reactions (field 1504)(including detailed information in the As Reported, Preferred Term, High Level Term, and High Level Group Term categories); Concomitant Drugs (field 1505) (each listed by Name, Dose, Route, and Suspect Status); Outcomes (field 1506); Manufacturer Control Code (field 1507); Manufacturer Date (field 1508); Adverse Event Date (field 1509); Report Type (field 1510); Report Source (field 1511); Case Source (field 1512), and Narrative (field 1513), if any. All data, including lab test and genetic information can be encoded and displayed.

It will be appreciated that the above-identified information is not the only information that can be provided; extra information fields may be also provided.

Figure 16B:
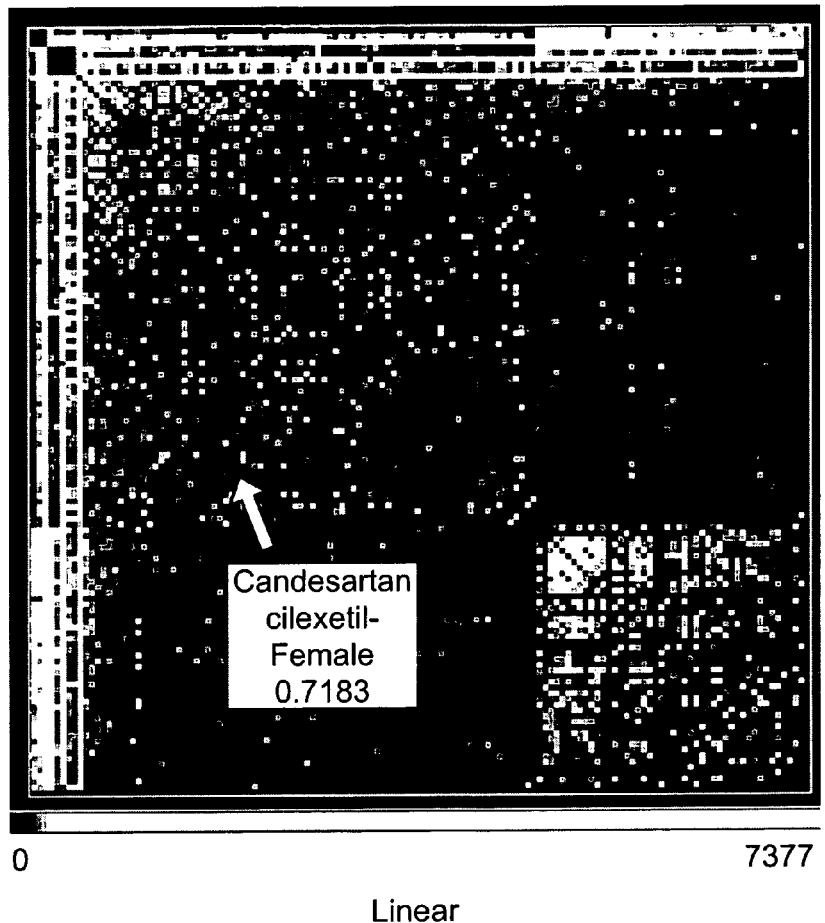
FIG. 16 is an exemplary illustration of a radar screen display of the present invention.

The adverse effect analysis result of the present invention are preferably presented in a format that provides both traditional tabular displays (line listings) and innovative "radar-like" displays. By populating a radar screen with textual information, a user moves from the cumbersome reading of printouts to the instant perception of correlations directly on the screen. Once a signal is identified, a case browser permit a user to move through user-defined sorting to the key cases involved. Once again the synergistic aspects of the invention come into play. A "Therapeutic Category" or "Labeled Reaction" selector can group the data on the radar screen to enhance the signal. An exemplary radar screen display is presented in FIG. 16.

The proportional analyzer engine of the present invention monitors outliers among reactions for drugs, for example, by comparing drugs to all drugs or those in a therapeutic class. The proportional analyzer engine can employ a variety of algorithms, including, but not limited to, proportion repeating ratio (PRR), ODDS ratio, and proportional reduction of error (PRE), among others.

The proportional analyzer is preferably invoked from the home screen. A user is, in a preferred embodiment, prompted to select a therapeutic category for analysis by the proportional analyzer engine. Alternatively, a drug or a drug set can be selected. A user can select the therapeutic category that contains the drug he/she wishes to analyze. Bayesian filtering is preferably available as an option to remove noisy results due to lower case counts from the analysis.

In a preferred embodiment of the present invention, a user is prompted as to how he/she would like to analyze the drugs and reactions against the reaction counts of all drugs in the system, or only against their peers in their therapeutic category. The invention again allows cross-operation of its elements. So, for example, a set of cases can be filtered to use a background for the proportional analysis or a specific case set can be defined.

Upon completion of the proportional analysis, a proportional analysis screen preferably presents the results. An exemplary proportional analysis screen is presented in FIG. 17. As presented in the figure, this screen preferably has several components, including, but not limited to a matrix showing the results for the relative ratios; a data block; and a line listing of the highest 100 relative ratios.

Preferably the proportional analysis screen presents the results of the analysis as a colored matrix of cells, indicating the frequency of reactions to various drugs compared to their expected normal frequency. The variation is either more or less frequent than expected, and the colors of the cells reflect the amount by which the observed number of reactions differs from the expected amount. Cells that are more darkly colored indicate reaction reporting lower than expected; cells that are gray indicate an as-expected value (or a Relative Ratio (RR) of 1); and cells that are more brightly colored indicate a greater Relative Ratio; the "hotter" the color (yellow to orange to red), the higher the frequency of reactions.

Figure 18:
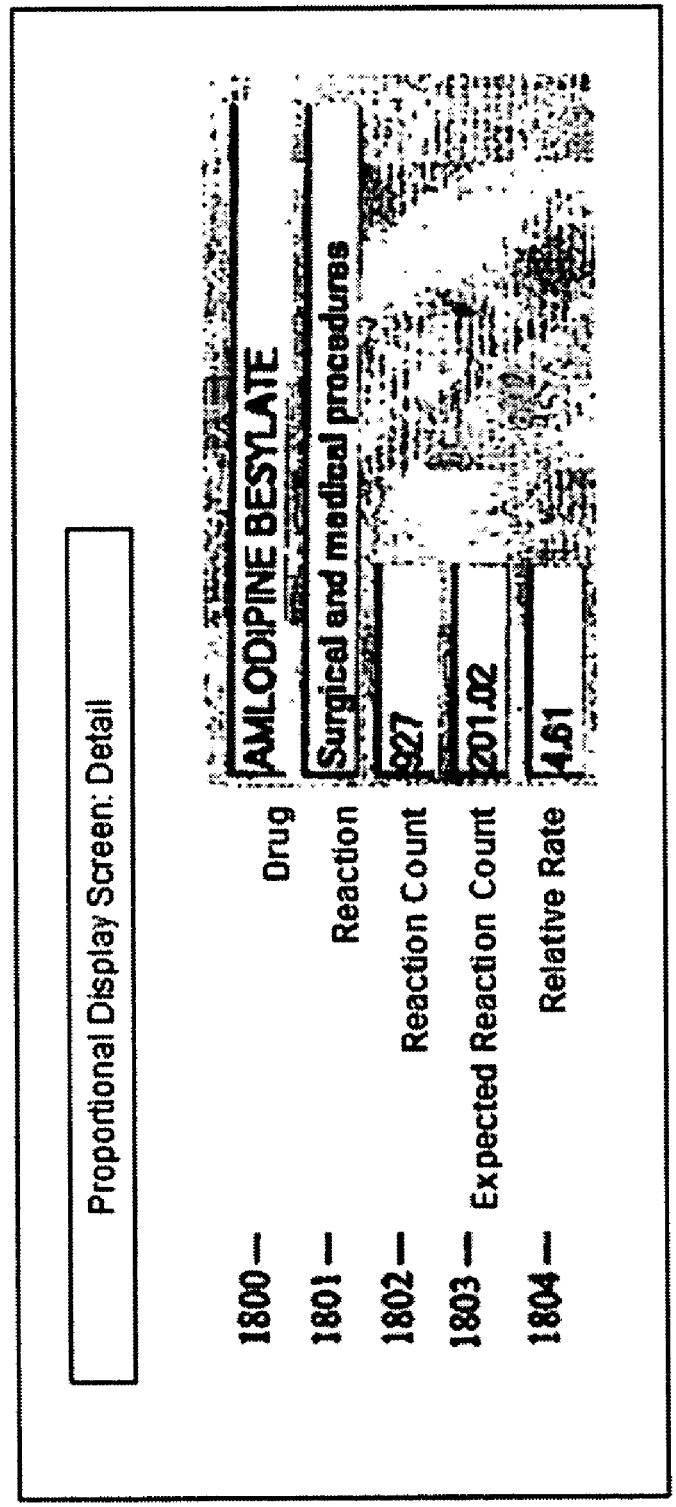
FIG. 18 is a representation of a proportional analysis results screen of the present invention.

A user may preferably select any cell in the matrix for further information. Selecting a specific cell provides details about the drug (field 1800) and its reaction (field 1801), including also the reaction count (field 1802), the expected reaction count (field 1803), and the Relative Ratio between the two (field 1804). An example of the proportional analysis results screen is provided in FIG. 18.

The invention also allows "analytical drill down". That is, the ability to redo the analysis, in a preferred case, for a drug and a reaction system-organ-class. The user then selects the level (e.g., PT) for re-analysis and is given the results in real time. The user can then iterate between high level and detail. It will be appreciated that the invention is not restricted to drug and reaction dimensions for proportional analysis. All pairs of the dimensions of the analytical engine (for example, reaction and outcomes) can be analyzed. Even within the cases of a single drug, the reactions and concomitant drugs could be proportionally analyzed.

Figure 19:
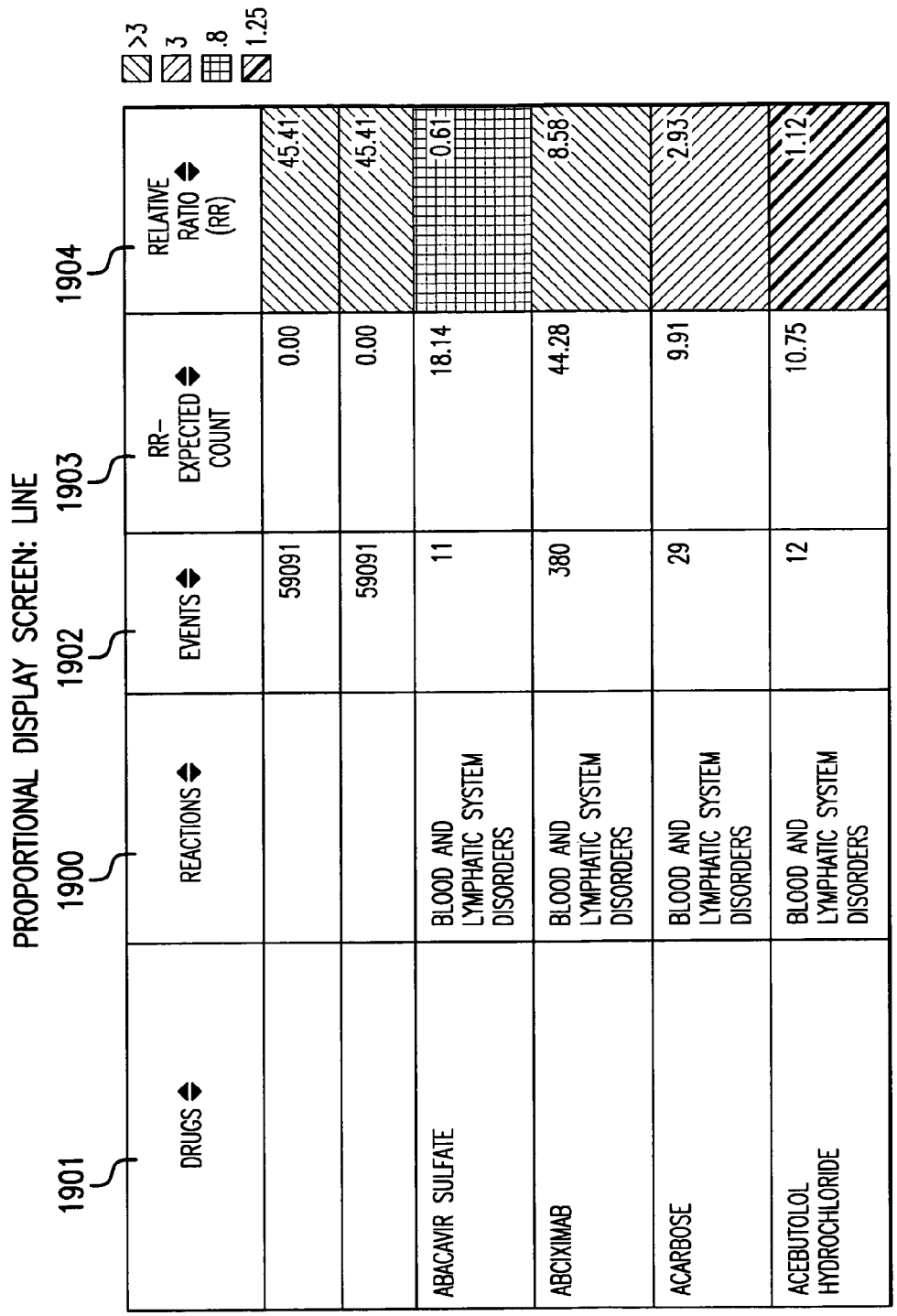
FIG. 19 is a depiction of a tabular version of a proportional analysis screen of the present invention.

In addition to the graphic display, the proportional analyzer also shows these data in a tabular form. FIG. 19 is the tabular presentation of the proportional analysis results. In this table, the location of the drug (field 1901) and its reaction (field 1900) in the matrix are indicated by numbers for row and column, row indicating the reaction and column signifying the drug of interest. The remaining three columns in the table preferably indicate the reaction count (field 1902)(with a hyperlink to the cases themselves), the expected reaction count (field 1903), and the Relative Ratio (field 1904). The entries are ranked in descending order, with the highest ratios listed first. The columns can preferably be sorted by clicking on their headings.

As in all tables, from the selector to the correlator, numbers are hyperlinked to the case-list. In the proportional analysis engine, all HLTs are available.

Figures 1, 20A:
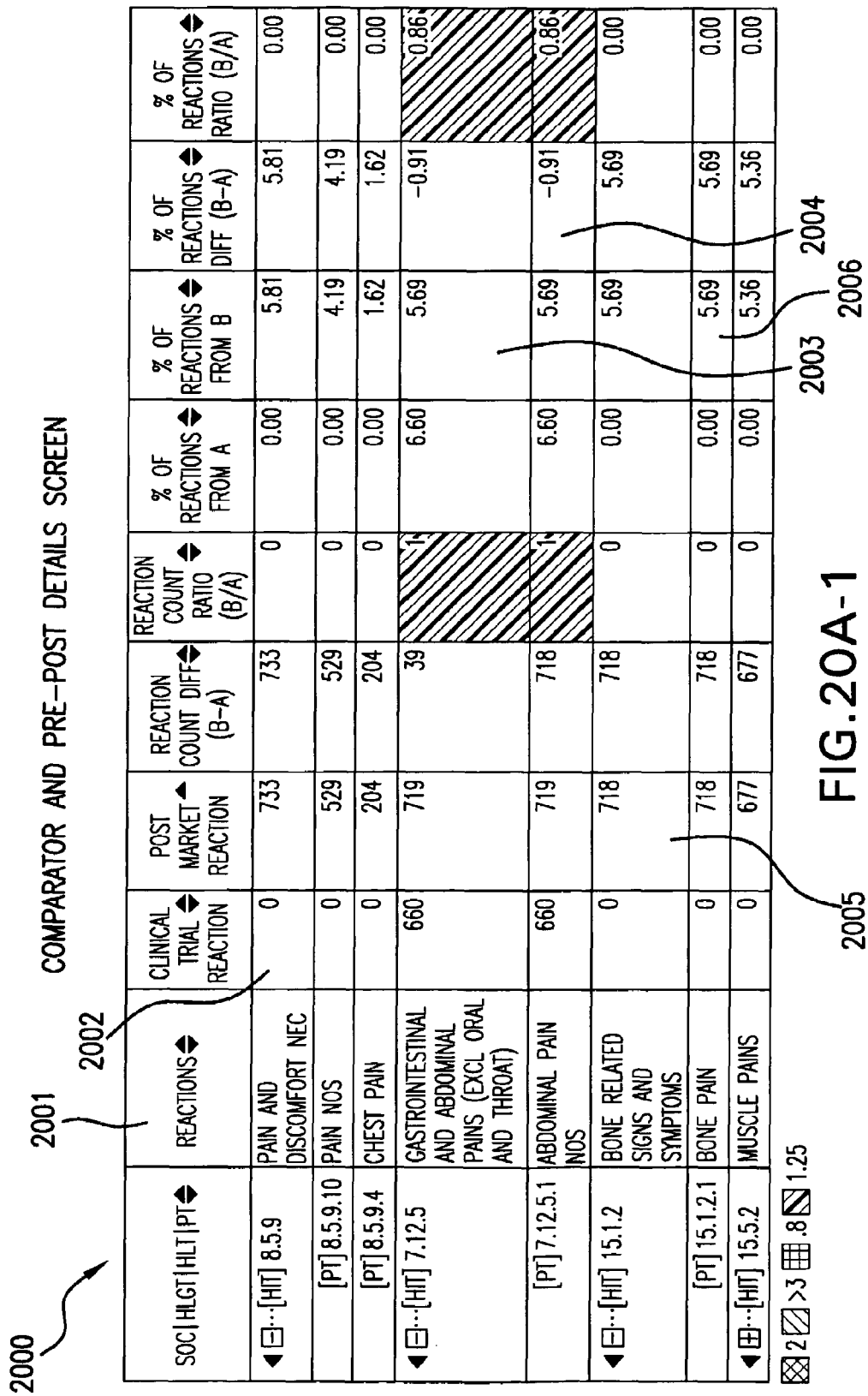

The comparator or differencing engine screen in the preferred offering offers three sets of analyzed data: Pre/Post Market data, Other Post-Market Reaction, and Other Clinical Trial Reaction. An exemplary comparator screen is provided in FIG. 20. The Pre/Post Market data is preferably organized into a series of columns in a first table (field 2000), providing the information, including Reaction HLT (field 2001); Clinical Trial Reaction (field 2002); Clinical Trial Percentage (field 2003), Clinical Trial Adjusted Percentage (field 2004); Post Market Reaction (field 2005); Post Market Percentage (field 2006); Post Market Adjusted Percentage (field 2007); and Difference Ratio (field 2008). The adjusted percentages account for proportions of those reactions that are common in both pre- and post-market reporting. The second table (field 2009) lists Other Post-Market Reaction (field 2010) and each reaction's Post-Market Percentage (field 2011). This information represents data available in the integrated public database. The third table (field 2012) provides Other Clinical Trial Reaction (field 2013) and each reaction's Clinical Trial Percentage (field 2014). This information indicates whether this reaction was mentioned on the manufacturer's package insert.

The comparator engine of the present invention is a differencing engine that is applied to measuring one drug's reactions, both pre- and post-market. This engine is essentially a "proportion of proportions" and is preferably limited to situations where: labeled adverse effect data can be quantified, terms can be mapped to MedDRA, and a useful number of reports are available for reactions, both pre- and post-market. The comparator can compare any two sets of cases for any two dimensions.

In viewing the results of the system and method of the present invention, when a box on a table or in a matrix or a hyperlink is selected, the case listing is generated. When a user clicks on any of the numbers, he/she is provided with a listing of each of the cases corresponding to that link. An exemplary Case List is provided in FIG. 21. For each case, various information is provided, including case ID (field 2100), gender (field 2101), Manufacturer Control Code (field 2102), FDA Report Receipt Date (field 2103), Age (field 2104), Drugs (field 2105), Reactions (field 2106), Seriousness (field 2107)(Y/N or normal outcome (optional)). These columns can be sorted by clicking on their headings. If a user selects a summary view, a profile of the cases in the case list is then calculated and displayed. Additionally, if a user wishes to learn the details of a specific case, he/she can click on the case ID number of any specific case on the correlation details screen.

This Case Details screen provides detailed information on each specific case. In addition to standard information such as the patient's case ID, gender, and age, it also includes Reactions (including detailed information in the As Reported, Preferred Term, High Level Term, and High Level Group Term categories); Concomitant Drugs (each listed by Name, Dose, Route, and Suspect Status); Outcomes; Manufacturer Control Code; Manufacturer Date; Adverse Event Date; Report Type; Report Source; Case Source; and Narrative, if any. As will be appreciated, additional details can be provided. If these details are structured, all features of the invention are expandable to that dimension. If the information is unstructured, the invention can extract and structure the data using the dictionary and thesaurus facilities.

It will appreciated that the system and method of the present invention has applications in risk assessment other than in the context of drug safety. For example, the system and method of the present invention can be used to analyze the causal elements of other events, for example, death or hospitalization, with regard to the other dimensions of the invention. Additionally, the system and method of the present invention can be similarly applied to other problems of signal detection and correlation where signals emerge in a large population with many dimensions. In general, the invention is applicable to any situation where there are reports (cases), primary elements (drugs, tires), means for measuring events (rash, discoloration), outcomes (death, blow out) and unrelated dimensions (age, temperature).

It will further be appreciated that the system and method of the present invention has applications in risk assessment in the fields of demographics, phenotype, genotype, genomics, and proteomics. Specifically, the system and method of the present invention can be used assess the risk/susceptibility of an individual or a group of a possible outcome (for example, lung cancer, leukemia, Jacob-Kreutzfeld syndrome) based on phenotype, genotype, or environmental exposure. The system and method of the present invention permits a user to assess the correlation between a possible outcome and multiple dimensions of an individual or a group.

Various preferred embodiments of the invention have been described in fulfillment of the various objects of the invention. It should be recognized that these embodiments are merely illustrative of the principles of the invention. Numerous modifications and adaptations thereof will be readily apparent to those skilled in the art without departing from the spirit and scope of the present invention.

The invention claimed is:

1. A computer system for assessing and analyzing risks of adverse effects resulting from use of at least one substance of interest, comprising:
    a selector for identifying at least one substance of interest;
    a profiler for selecting from multiple profiles related to safety of the at least one substance of interest, using at least one filter to determine at least one set of cases;
    at least one data mining engine for processing the at least one set of cases determined and submitted by the at least one filter; and
    an output device for displaying analytic results from the data mining engine,
    wherein the substance of interest is assessed in combination with other drugs, foodstuffs, beverages, nutrients, vitamins, toxins, chemicals, hormones, and supplements;
    wherein the at least one data mining engine comprises a correlator to look for correlated signal characteristics in at least one of drug information, reaction information and demographic information;
    wherein the correlator is configured to maintain a consistent vocabulary by processing a vector comprising a plurality of categorical terms; and
    wherein the plurality of categorical terms sent to the correlator are therapeutic categories.

2. The computer system for assessing and analyzing risks of adverse effects resulting from use of at least one substance of interest according to claim 1, wherein the at least one data mining engine also comprises a proportional analysis engine to assess deviations in a set of reactions to the at least one substance of interest.

3. The computer system for assessing and analyzing risks of adverse effects resulting from use of at least one substance of interest according to claim 1, wherein the at least one data mining engine also comprises a comparator to measure reactions to the at least one substance of interest against a user-defined backdrop.

4. The computer system for assessing and analyzing risks of adverse effects resulting from use of at least one substance of interest according to claim 1, wherein the data mining engine is at least two members of the group consisting of a proportional analysis engine, a comparator, and a correlator.

5. The computer system for assessing and analyzing risks of adverse effects resulting from use of at least one substance of interest according to claim 1, wherein the system permits assessment and analysis of risks of adverse effects resulting from use of at least one substance of interest in any of multiple dimensions of risk assessment and analysis.

6. A computer system for assessing and analyzing risks of adverse effects resulting from use of at least one drug of interest, comprising:
   a selector for identifying at least one drug of interest;
   a profiler for selecting from multiple profiles related to safety of the at least one drug of interest, using at least one filter to determine at least one set of cases;
   at least one data mining engine for processing the at least one set of cases determined and submitted by the at least one filter; and
   an output device for displaying analytic results from the data mining engine,
   wherein the drug of interest is assessed in combination with other drugs, foodstuffs, beverages, nutrients, vitamins, toxins, chemicals, hormones, and supplements;
   wherein the at least one data mining engine comprises a correlator to look for correlated signal characteristics in at least one of drug information, reaction information and demographic information;
   wherein the correlator is configured to maintain a consistent vocabulary by processing a vector comprising a plurality of categorical terms; and
   wherein the plurality of categorical terms sent to the correlator are therapeutic categories.

7. The computer system for assessing and analyzing risks of adverse effects resulting from use of at least one drug of interest according to claim 6, wherein the at least one data mining engine also comprises a proportional analysis engine to assess deviations in a set of the reactions to the drug of interest.

8. The computer system for assessing and analyzing risks of adverse effects resulting from use of at least one drug of interest according to claim 6, wherein the at least one data mining engine also comprises a comparator to measure reactions to the drug of interest against a user-defined backdrop.

9. The computer system for assessing and analyzing risks of adverse effects resulting from use of at least one drug of interest according to claim 6, wherein the data mining engine is at least two members of the group consisting of a proportional analysis engine, a comparator, and a correlator.

10. The computer system for assessing and analyzing risks of adverse effects resulting from use of at least one drug of interest according to claim 6, wherein the system permits assessment and analysis of risks of adverse effects resulting from use of at least one drug of interest in any of multiple dimensions of risk assessment and analysis.

11. The computer system of claim 6, wherein the proportional analysis further comprises comparing the drug of interest to a second drug of interest in a same therapeutic category for the drug of interest selected.

12. The computer system of claim 6, wherein the proportional analysis further comprises comparing the drug of interest to a second drug of interest in a second therapeutic category.

13. The computer system of claim 6, further comprising:
   a Bayesian filtering, wherein the Bayesian filtering includes providing a statistical cut-off threshold to reduce the effect of drugs or reactions accounting for less than a certain percentage of cases of adverse drug events.

14. The computer system of claim 6, further comprising:
   comparing clinical trial data, wherein the comparison includes comparing the potential and actual adverse effects of the drug of interest in a pre-market environment to that of the potential and actual adverse effects of the drug of interest in a post-market environment.

15. A computer-implemented method for assessing and analyzing risks of adverse effects resulting from use of at least one substance of interest, comprising:
   identifying the at least one substance of interest;
   selecting a profile of the at least one substance of interest related to safety of the at least one substance of interest, using at least one filter to determine at least one set of cases;
   analyzing risks of adverse effects resulting from use of the at least one substance of interest using at least one data mining engine for processing the at least one set of cases determined and submitted by the at least one filter, wherein the at least one data mining engine comprises a correlator to look for correlated signal characteristics in at least one of drug information, reaction information and demographic information;
   maintaining a consistent vocabulary by using the correlator to process a vector comprising a plurality of categorical terms; and
   displaying results from analyzing risks of adverse effects resulting from the use of the at least one substance of interest,
   wherein the plurality of categorical terms sent to the correlator are therapeutic categories.

16. The computer-implemented method for assessing and analyzing risks of adverse effects resulting from use of at least one substance of interest according to claim 15, wherein the at least one data mining engine also comprises a proportional analysis engine to assess deviations in a set of the reactions to the at least one substance of interest.

17. The computer-implemented method for assessing and analyzing risks of adverse effects resulting from use of at least one substance of interest according to claim 15, wherein the at least one data mining engine also comprises a comparator to measure reactions to the at least one substance of interest against a user-defined backdrop.

18. The computer-implemented method for assessing and analyzing risks of adverse effects resulting from use of at least one substance of interest according to claim 15, wherein the data mining engine is at least two members of the group consisting of a proportional analysis engine, a comparator, and a correlator.

19. The computer-implemented method for assessing and analyzing risks of adverse effects resulting from use of at least one substance of interest according to claim 15, wherein the at least one substance of interest is assessed in combination with other drugs, foodstuffs, beverages, nutrients, vitamins, toxins, chemicals, hormones, and supplements.

20. The computer-implemented method for assessing and analyzing risks of adverse effects resulting from use of at least one substance of interest according to claim 15, wherein the method permits assessment and analysis of risks of adverse effects resulting from use of at least one substance of interest in any of multiple dimensions of risk assessment and analysis.

21. A computer-implemented method for assessing and analyzing risks of adverse effects resulting from use of at least one drug of interest, comprising:
- identifying the at least one drug of interest, as well any other drugs, nutrients, supplements, and other substances;
- selecting a profile of the at least one drug of interest related to safety of the at least one drug of interest, using at least one filter to determine at least one set of cases;
- analyzing risks of adverse effects resulting from use of the at least one drug of interest using at least one data mining engine for processing the at least one set of cases determined and submitted by the at least one filter, wherein the at least one data mining engine comprises a correlator to look for correlated signal characteristics in at least one of drug information, reaction information and demographic information;
- maintaining a consistent vocabulary by using the correlator to process a vector comprising a plurality of categorical terms; and
- displaying results from analyzing risks of adverse effects resulting from the use of the at least one drug of interest,
- wherein the at least one drug of interest is assessed in combination with other drugs, foodstuffs, beverages, nutrients, vitamins, toxins, chemicals, hormones, and supplements; and
- wherein the plurality of categorical terms sent to the correlator are therapeutic categories.

22. The computer-implemented method for assessing and analyzing risks of adverse effects resulting from use of at least one drug of interest according to claim 21, wherein the at least one data mining engine also comprises a proportional analysis engine to assess deviations in a set of the reactions to the at least one drug of interest.

23. The computer-implemented method for assessing and analyzing risks of adverse effects resulting from use of at least one drug of interest according to claim 21, wherein the at least one data mining engine also comprises a comparator to measure reactions to the at least one drug of interest against a user-defined backdrop.

24. The computer-implemented method for assessing and analyzing risks of adverse effects resulting from use of at least one drug of interest according to claim 21, wherein the data mining engine is at least two members of the group consisting of a proportional analysis engine, a comparator, and a correlator.

25. The computer-implemented method for assessing and analyzing risks of adverse effects resulting from use of at least one drug of interest according to claim 21, wherein the method permits assessment and analysis of risks of adverse effects resulting from use of at least one drug of interest in any of multiple dimensions of risk assessment and analysis.

26. A computer system for assessing and analyzing risks of adverse effects resulting from use of at least one substance of interest, comprising:
- a selector for identifying at least one substance of interest;
- a profiler for selecting from multiple profiles related to safety of the at least one substance of interest, using at least one filter to determine at least one set of cases;
- at least one data mining engine for processing the at least one set of cases determined and submitted by the at least one filter; and
- an output device for displaying analytic results from the data mining engine,
- wherein the substance of interest is assessed in combination with other drugs, foodstuffs, beverages, nutrients, vitamins, toxins, chemicals, hormones, and supplements,
- wherein the assessment of the substance of interest includes comparing the potential and actual adverse effects of a substance of interest in a pre-market environment to that of the potential and actual adverse effects of a substance of interest in a post-market environment;
- wherein the at least one data mining engine comprises a correlator to look for correlated signal characteristics in at least one of drug information, reaction information and demographic information;
- wherein the correlator is configured to maintain a consistent vocabulary by processing a vector comprising a plurality of categorical terms; and
- wherein the plurality of categorical terms sent to the correlator are therapeutic categories.

27. The computer system for assessing and analyzing risks of adverse effects resulting from use of at least one substance of interest according to claim 26,
- wherein the substance of interest identified by the selector is a target drug;
- wherein the target drug is profiled in relation to a one or more concomitant drugs;
- wherein the profiler identifies one or more concomitant drug dimensions;
- wherein the one or more concomitant drugs were prescribed in one or more cases where the target drug was also prescribed;
- wherein the one or more prescriptions are configured to result in an adverse drug reaction report; and
- wherein the adverse drug reaction is configured so as to be reported in an adverse effects reporting database.

28. The computer system for assessing and analyzing risks of adverse effects resulting from use of at least one substance of interest according to claim 27,
- wherein the profiler is configured to label each of the one or more drugs as a suspect drug or a non-suspect drug;
- wherein the profiler is configured to analyze a patient information, the patient information further comprising a plurality of categories for patients whose information is reported in an adverse drug effects reporting database;
- wherein the plurality of categories analyzed includes a plurality of age groups, a male gender, a female gender, and a plurality of ages between 16 years old and 75 years old.

29. The computer system for assessing and analyzing risks of adverse effects resulting from use of at least one substance of interest according to claim 28,
- wherein the display is configured to show the one or more drugs labeled as a suspect drug or a non-suspect drug;
- wherein the display is configured to present a report showing the number of adverse drug effect event reports in each year during a decade;
- wherein a drug detail section of the report involves paging and sorting;
- wherein the report is configured to be broken down into individual years of birth of a patient who experienced an adverse drug effect reported in an adverse drug effects reporting database;
- wherein the report is configured to show a plurality of serious outcomes;
- wherein the report is configured to show serious outcomes in the report in a plurality of colors;

wherein the report is configured to provide a table of outcomes, a count, and percentages of the outcomes in each category;

wherein the report is configured to present a total number of serious outcomes and a total number of non-serious outcomes.

30. The computer system for assessing and analyzing risks of adverse effects resulting from use of at least one substance of interest according to claim 26, wherein the filtering is configured to be applied individually, as a group, and globally;

wherein the filtering is configured to be retained for later use;

wherein the filtering is configured to be applied repeatedly;

wherein two or more filters are configured to be merged;

wherein the filter is configured to be overwritten; and wherein the filter is configured to be saved as an incremental filter.

31. The computer system for assessing and analyzing risks of adverse effects resulting from use of at least one substance of interest according to claim 26, further comprising:

a pre-filter, wherein the pre-filter is configured in a first state to switch on an indication-related adverse drug reaction and wherein the pre-filter is configured in a second state to switch off an indication-related adverse drug reaction.

32. The computer system for assessing and analyzing risks of adverse effects resulting from use of at least one substance of interest according to claim 26, wherein the analysis is configured to search for a signal;

wherein the signal is selected from among the group consisting of an anomaly in a random population reported in an adverse effects reporting database, a change against a known background, or a coherent target in a noise background; and wherein the signal is detected by a proportional analysis engine, a differencing engine, and the correlator.

33. The computer system for assessing and analyzing risks of adverse effects resulting from use of at least one substance of interest according to claim 32, wherein the correlator is configured to measure a degree of an association according to a correlation algorithm;

wherein the correlator is configured to rank a first pair of terms relative to a second pair of terms;

wherein the correlator is configured to calculate a strength of the association for a known factor and for a rare adverse drug effect; and wherein the display presents the results of a correlated search.

34. The computer system for assessing and analyzing risks of adverse effects resulting from use of at least one substance of interest according to claim 33, wherein the association is a drug and a reaction or a patient age and an outcome.

35. The computer system for assessing and analyzing risks of adverse effects resulting from use of at least one substance of interest according to claim 26, wherein the correlator is configured to use the Pearson product-moment correlation.

* * * * *